(12) United States Patent
Pehla et al.

(10) Patent No.: US 12,265,092 B2
(45) Date of Patent: *Apr. 1, 2025

(54) WORKFLOW FOR RISK ASSESSMENT AND PATIENT MANAGEMENT USING PROCALCITONIN AND MIDREGIONAL-PROADRENOMEDULLIN

(71) Applicant: B.R.A.H.M.S GmbH, Hennigsdorf (DE)

(72) Inventors: Aline Pehla, Birkenwerder (DE); Darius Wilson, Berlin (DE)

(73) Assignee: B.R.A.H.M.S GMBH, Hennigsdorf (DE)

( * ) Notice: Subject to any disclaimer, the term of this patent is extended or adjusted under 35 U.S.C. 154(b) by 434 days.

This patent is subject to a terminal disclaimer.

(21) Appl. No.: 16/956,036

(22) PCT Filed: Dec. 20, 2018

(86) PCT No.: PCT/EP2018/086150
§ 371 (c)(1),
(2) Date: Jun. 19, 2020

(87) PCT Pub. No.: WO2019/122100
PCT Pub. Date: Jun. 27, 2019

(65) Prior Publication Data
US 2021/0109117 A1    Apr. 15, 2021

(30) Foreign Application Priority Data

Dec. 20, 2017  (EP) .................................. 17209151

(51) Int. Cl.
*G01N 33/74*    (2006.01)
(52) U.S. Cl.
CPC ....... *G01N 33/74* (2013.01); *G01N 2333/585* (2013.01); *G01N 2800/26* (2013.01); *G01N 2800/52* (2013.01)
(58) Field of Classification Search
None
See application file for complete search history.

(56) References Cited

U.S. PATENT DOCUMENTS

| | | |
|---|---|---|
| 7,915,002 B2 | 3/2011 | Bergmann |
| 7,939,639 B2 | 5/2011 | Cuttitta et al. |
| 8,507,210 B2 | 8/2013 | Bergmann et al. |
| 9,229,013 B2 | 1/2016 | Bergmann et al. |
| 9,541,549 B2 | 1/2017 | Bergmann et al. |
| 2010/0292131 A1 | 11/2010 | Kas et al. |
| 2011/0086831 A1 | 4/2011 | Bergmann et al. |
| 2012/0094314 A1 | 4/2012 | Bahrami et al. |
| 2013/0203612 A1 | 8/2013 | Graf et al. |
| 2013/0302841 A1 | 11/2013 | Struck et al. |
| 2015/0011017 A1 | 1/2015 | Bergmann et al. |
| 2017/0010286 A1 | 1/2017 | Bergmann |
| 2017/0370949 A1 | 12/2017 | Struck et al. |
| 2018/0348235 A1 | 12/2018 | Viguéet al. |
| 2019/0178894 A1 | 6/2019 | Ziera et al. |
| 2019/0376985 A1 | 12/2019 | Bergmann et al. |
| 2021/0156850 A1 | 5/2021 | Anderberg et al. |

FOREIGN PATENT DOCUMENTS

| | | |
|---|---|---|
| EP | 1488209 B1 | 12/2005 |
| EP | 2320237 B1 | 8/2016 |
| WO | 9707214 A1 | 2/1997 |
| WO | 0242770 A1 | 5/2002 |
| WO | 04090546 A1 | 10/2004 |
| WO | 08012019 A2 | 1/2008 |
| WO | WO09062948 A1 | 5/2009 |
| WO | 10128071 A1 | 11/2010 |
| WO | 10139475 A1 | 12/2010 |
| WO | 12059477 A1 | 5/2012 |
| WO | 13086359 A1 | 6/2013 |
| WO | 14147153 A1 | 9/2014 |
| WO | 17089474 A1 | 6/2017 |
| WO | 18007588 A1 | 1/2018 |
| WO | 18029214 A1 | 2/2018 |

OTHER PUBLICATIONS

International Search Report dated Feb. 25, 2019 issued in corresponding PCT/EP2018/086150 application (6 pages).
S. Angeletti et al., "Diagnostic and Prognostic Role of Procalcitonin (PCT) and MR-Pro-Adrenomedullin (MR-proADM) in Bacterial Infections", APMIS, vol. 123, No. 9 (2015) pp. 740-748.
P.E. Charles et al., "MR-ProADM Elevation Upon ICU Admission Predicts The Outcome of Septic Patients and is Correlated With Upcoming Fluid Overload", Shock, vol. 48, No. 4 (2017) pp. 418-426.
G. Elke et al., "The Use of Mid-Regional Proadrenomedullin to Identify Disease Severity and Treatment Response to Sepsis—A Secondary Analysis of a Large Randomised Controlled Trial", Critical Care, vol. 22, No. 1 (2018) pp. 1-12.
D. Andaluz-Ojeda et al., "Superior Accuracy of Mid-Regional Proadrenomedullin for Mortality Prediction in Sepsis with Varying Levels of Illness Severity", Intensive Care, vol. 7 (2017) pp. 1-8.

(Continued)

*Primary Examiner* — Elizabeth C. Kemmerer
(74) *Attorney, Agent, or Firm* — MILLEN, WHITE, ZELANO & BRANIGAN, P.C.; Ryan R. Pool

(57) ABSTRACT

The present invention is in the field of clinical diagnostics. Particularly, the present invention relates to the assessment of severity of a subject being suspected of an infection or having an infection, who may have physiological signs or increased risk factors for infection, in particular from an infectious disease by determination of the levels of Procalcitonin (hereinafter: PCT) (SEQ ID No: 1 and/or proadrenomedullin (hereinafter: proADM)) (SEQ ID No: 3) or a partial peptide or fragment thereof, in particular midregional proadrenomedullin (MR-proADM) (SEQ ID No: 2), in a sample of a patient and the invention is related to a workflow hereto. Moreover, the invention refers to the assessment related to an infection like ruling out/in a patient and stratification, risk assessment, in particular to avoid rehospitalisation and hospital and post-discharge mortality.

8 Claims, 7 Drawing Sheets
Specification includes a Sequence Listing.

(56) References Cited

OTHER PUBLICATIONS

K. Saeed et al., "The Early Identification of Disease Progression in Patients with Suspected Infection Presenting to the Emergency Department: A Multi-Centre Derivation and Validation Study", Critical Care, vol. 23, No. 1 (2019) pp. 1-15.
Anadaluz-Ojeda D. et al. : "Superior accuracy of mid-regional proadrenomedullin for mortality prediction in sepsis with varying levels of illness severity", Intensive Care, vol. 7, Feb. 10, 2017, Article No. 15, pp. 1-8.
Angeletti S. et al. : "Diagnostic and prognostic role of procalcitonin (PCT) and MR-pro-Adrenomedullin (MR-proADM) in bacterial infections", APMIS, vol. 123, No. 9, Jun. 8, 2015 (Jun. 8, 2015), pp. 740-748.
Angeletti S. et al.: "Procalcitonin and mid-regional pro-adrenomedullin test combination in sepsis diagnosis", Clinical Chemistry and Laboratory Medicine, De Gruyter, De, vol. 51, No. 5, Apr. 30, 2013 (Apr. 30, 2013), pp. 1059-1067, XP009502330, ISSN: 1434-6621, DOI: 10.1515/CCLM-2012-0595.
Bruno Viaggi et al.: "Mid regional pro-adrenomedullin for the prediction of organ failure in infection. Results from a single centre study", Plos One, vol. 1 3, No. 8, Aug. 13, 2018 (Aug. 13, 2018), p. e0201491, xP055535888, DOI : 1 D137 1/journal.pone.0201 491.
Cairon Pietr—et al: "Circulating Biologically Active Adrenomedullin such statement (bio-ADM) Predicts Hemodynamic support Requirement and Mortality During Sepsis", Chest, vol. 152, No. 2, Aug. 1, 2017 (Aug. 1, 2017), pp. 312-320, XP55430860.
Caroline Guignant et al: "Assessment of pro-vasopressin and proadrenomedullin as predictors of 28-day mortality in septic shock patients", Intensive Care Medicine, vol. 35, No. 1 1 , Aug. 7, 2009 (Aug. 7, 2009), pp. 1859-1867, xP055535903, De Issn: 0342-4642, DOI: 10.1 007is001 34-009-1 610-5.
Charles P.-E. et al: "MR-ProADM elevation upon ICU admission predicts the outcome of septic patients and is correlated with upcoming fluid overload", Shock, vol. 48, No. 4, Oct. 2017, pp. 418-426.
Christ-Crain M. Ei Al: "Biomarkers in respiratory tract infections: diagnostic guides to antibiotic prescription, prognostic markers and mediators", European Respiratory Journal, Munksgaard International Publishers, Copenhagen, DK, vol. 30, No. 3, Aug. 31, 2007 (Aug. 31, 2007), pp. 556-573, XP00950261 1.
Christ-Crain M.: "Procalcitonin Guidance of Antibiotic in Community—acquired Pneumonia: A Randomized Trial", American Journal of Respiratory Critical Care Med-Cine, vol. 174, no. (Jan. 1, 2006), pp. 84-93, XP055021 728, ISSN: 1 073 -449X, DOI: 10.11 64/rccm. 200512-1 9220C.
Christ-Crain Mirjam et al: "Mid-regional proadrenomedullin as a prognostic marker in sepsis: an study ", Critical Care, Biomed Central London, GB, vol. 9, No. 6, Nov. 15, 2005 (Nov. 15, 2005), pp. R81 6-R824, XP021012417, ISSN: 1364-8535, DOI: 10.11 86/CC3885.
De Jong Evelien Ei Al: "Efficacy and safety of procalcitonin guidance in reducing the duration of antibiotic treatment—n critically patients: a randomised, controlled, open-label trial", Lancet Infectious Diseases, Elsevier Lid, US, vol. 16, No. 7,Mar. 2, 2016 (Mar. 2, 2016), pp. 819-827, XP02961 8593.
De La Torre-Prados Maria V et al: "Mid-regional proadrenomedullin as prognostic biomarker in septic shock", Minerva Anestes—Olog-Ca G—Ornale Italiano Di Anestesia E D—Analg, Societa Italiana Di an Estesiolog Ia, IT, vol. 82, No. 7, Jul. 1, 2016 (Jul. 1, 2016), pp. 760-766, XP0091 92235, ISSN 1827-1596.
Elke G. et al.: "The use of mid-regional proadrenomedullin to identify disease severity and treatment response to sepsis—a secondary analysis of a large randomised controlled trial", Crit. Care, vol. 22, No. 1, 79, Mar. 21, 2018 (Mar. 21, 2018), pp. 1-12, XP55556348.
Gille Jochen et al: "MR-proADM: A New Biomarker for Early Diagnosis of Sepsis in Burned Patients", Journal of Burn Care & Research, Williams & Wilkins, US, vol. 38, No. 5, Aug. 31, 2017 (Aug. 31, 2017), pp. 290-298, XP009502061.
Hartmann Oliver et al: "Time -dependent Cox regression: Serial measurement of the cardiovascular biomarker proadrenomedullin—mproves survival prediction in patients with -ower resp-ratory infection", International Journal of Cardiology, vol. 161, No. 3, Sep. 24, 2012, p. 166-173, XP028959234.
Michels M Ei Al: "High plasma mid-regional pro-adrenomedullin-evels in children with severe dengue virus—fections ", Journal of Clinical Virology, Elsevier, Amsterdam, NL, vol. 50, No. 1, Jan. 1, 2011 (Jan. 1, 2011), pp. 8-12, XP027588087.
Munirah Al Shuaibi et al: "Pro-adrenomedullin as a Novel Biomarker for Predicting Infections and Response to Antimicrobials in Febrile Patients With Hematologic Malignancies", Cli n ical Infectious Diseases, vol. 56, No. 7,Jan. 3, 2013 (Jan. 3, 2013), pp. 943-950, xP055535801, US ISSN: 1 058-4838, DOI: 10.1 O93icidicis1 029.
Pereira J.M. et al: "Mid-regional proadrenomedullin: An early marker of response in critically community-acquired pneumonia?", Revista Portugu Esa De Pneumologia (English Edition), vol. 22, No. 6, Nov. 1, 2016 (Nov. 1, 2016), pp. 308-314, XP0554451 19, ISSN: 2173-5115, DOI: 10.1016/j.rppnen.2016 .03.012.
Rossella Marino et al: "Plasma adrenomedullin is associated with short-term mortality and vasopressor requirement in patients admitted with sepsis", Critical Care, Biomed Central Ltd., London, GB, vol. 18, No. 1,Feb. 17, 2014 (Feb. 17, 2014), p. R34, XP021179720, ISSN: 1364-8535, DOI: 10.1 186/CC13731.
Saeed K. et al.: "The early identification of disease progression in patients with suspected infection presenting to the emergency department: a multi-centre derivation and validation study", Crit. Care, vol. 23, No. 1, 40, Feb. 8, 2019 (Feb. 8, 2019), pp. 1-15, XP55556343, the whole document.
Schuetz Philipp El AL: "Blood biomarkers for personalized treatment and patient management decisions in community-acquired pneumonia", Current Opinion on Infectious Diseases., vol. 26, No. 2, Apr. 1, 2013 (Apr. 1, 2013), pp. 159-167 , XP055439092.
Sebastian Decker et al: Immune—Response Patterns and Next Generation Sequencing Diagnostics for the Detection of Mycoses in Patients with Septic Shock-Results of a Combined Clinical and Experimental Investigation, International Journal of Molecular Sciences, vol. 18, No. 8, Aug. 18, 2017 (Aug. 18, 2017), p. 1796, XP055417185,DOI: 10.3390/ijm518081796.
Shuaibi M. Al et al.: "Pro-adrenomedullin as a Novel Biomarker for Predicting Infections and Response to Antimicrobials in Febrile patients With Hematologic Malignancies", Clinical Infectious Diseases, vol. 56, No. 7 ,Jan. 3, 2013, p. 943-950, XP055418326.
Siripen Kalayanarooj: "Clinical Manifestations and Management of Dengue/DHF /Dss", Tropical Medicine and Health, vol. 39, No. 4SUPPLEMENT , Jan. 1, 2011 (Jan. 1, 2011), pp. S83-S87, XP055511310.
Thanachartwet Vipa Ei Al: "Serum Procalcitonin and Peripheral Venous Lactate for Predicting Dengue Shock and/or Organ Failure: A Prospective Observational Study", Plos Neglected Tropical Diseases, vol. 10, No. 8, Aug. 26, 2016 (Aug. 26, 2016), p.e0004961, XP055511330.
Jeda et al: "Increased plasma levels of adrenomedullin in patients with systemic inflammatory response syndrome.", Amer. J Resp. Crit. Care Med., vol. 160, No. 1, Jul. 1, 1999, pp. 132-136, XP055052609.
Wang R L et al: "Prediction about severity and outcome of sepsis by pro-atrial natriuretic peptide and pro-adrenomedullin", Chin. J. Traumatol, NL, vol. 13, No. 3, Jun. 1, 2010, pp. 152-157, XP027087080.
Bello et al. Prognostic power of proadrenomedullin in community-acquired pneumonia is independent of aetiology. Eur Respir J 2012; 39: 1144-1155.
Cavallazzi et al. Midregional proadrenomedullin for prognosis in community-acquired pneumonia: a systematic review. Respiratory Medicine (2014) 108, 1569e1580.
Courtais et al. Proadrenomedullin, a useful tool for risk stratification in high Pneumonia Severity Index score community acquired pneumonia. American Journal of Emergency Medicine (2013) 31, 215-221.
Curbelo et al.Inflammation biomarkers in blood as mortality predictors in community-acquired pneumonia admitted patients: Impor-

(56) References Cited

OTHER PUBLICATIONS tance of comparison with neutrophil count percentage or neutrophil-lymphocyte ratio. Plos One | https://doi.org/10.1371/journal.pone.0173947 Mar. 16, 2017 (pp. 1-14).

Debiane et al. The utility of proadrenomedullin and procalcitonin in comparison to C-reactive protein as predictors of sepsis and bloodstream infections in critically ill patients with cancer. Crit Care Med. Dec. 2014 (pp. 1-9) DOI: 10.1097/CCM.0000000000000526.

Gordo-Remartínez. Usefulness of midregional proadrenomedullin to predict poor outcome in patients with community acquired pneumonia. Plos One | DOI:10.1371/journal.pone.0125212 Jun. 1, 2015 (pp. 1-15).

Hoeboer SH et al. Old and new biomarkers for predicting high and low risk microbial infection in critically ill patients with new onset fever: a case for procalcitonin. Journal of Infection (2012) 64, 484e493.

Huang et al. Midregional proadrenomedullin as a prognostic tool in community-acquired pneumonia. Chest / 136 / 3 / Sep. 2009 pp. 823.

Lundberg et al. Adrenomedullin and endothelin-1 are associated with myocardial injury and death in septic shock patients. Critical Care (2016) 20:178.

Renaud et al. Proadrenomedullin improves Risk of Early Admission to ICU score for predicting early severe community-acquired pneumonia. Chest / 142 / 6 / Dec. 2012 1447.

Schuetz P et al. Circulating precursor levels of endothelin-1 and adrenomedullin, two endothelium-derived, counteracting substances, in sepsis. Endothelium. Endothelium, 14:345-351, 2007.

Suberviola et al. Prognostic value of proadrenomedullin in severe sepsis and septic shock patients with community-acquired pneumonia. Swiss Med Wkly. 2012; 142:w13542.

Suberviola et al. Hospital mortality prognostication in sepsis using the new biomarkers suPAR and proADM in a single determination on ICU admission. Intensive Care Med 2013, pp. 1-12, DOI 10.1007/s00134-013-3056-z.

Travaglino F et al. Utility of Procalcitonin (PCT) and Mid regional pro-Adrenomedullin (MR-proADM) in risk stratification of critically ill febrile patients in Emergency Department (Ed). A comparison with Apache II score. BMC Infect Dis. Aug. 8, 2012 (pp. 1-8).

Figure 1: Workflow

SEQUENCE LISTING

<160> NUMBER OF SEQ ID NOS: 4

<210> SEQ ID NO 1
<211> LENGTH: 116
<212> TYPE: PRT
<213> ORGANISM: Homo sapiens

<400> SEQUENCE: 1

Ala Pro Phe Arg Ser Ala Leu Glu Ser Ser Pro Ala Asp Pro Ala Thr
1               5                   10                  15

Leu Ser Glu Asp Glu Ala Arg Leu Leu Leu Ala Ala Leu Val Gln Asp
            20                  25                  30

Tyr Val Gln Met Lys Ala Ser Glu Leu Glu Gln Glu Gln Glu Arg Glu
        35                  40                  45

Gly Ser Ser Leu Asp Ser Pro Arg Ser Lys Arg Cys Gly Asn Leu Ser
    50                  55                  60

Thr Cys Met Leu Gly Thr Tyr Thr Gln Asp Phe Asn Lys Phe His Thr
65                  70                  75                  80

Phe Pro Gln Thr Ala Ile Gly Val Gly Ala Pro Gly Lys Lys Arg Asp
                85                  90                  95

Met Ser Ser Asp Leu Glu Arg Asp His Arg Pro His Val Ser Met Pro
            100                 105                 110

Gln Asn Ala Asn
        115

<210> SEQ ID NO 2
<211> LENGTH: 48
<212> TYPE: PRT
<213> ORGANISM: Homo sapiens

<400> SEQUENCE: 2

Glu Leu Arg Met Ser Ser Tyr Pro Thr Gly Leu Ala Asp Val Lys
1               5                   10                  15

Ala Gly Pro Ala Gln Thr Leu Ile Arg Pro Gln Asp Met Lys Gly Ala
            20                  25                  30

Ser Arg Ser Pro Glu Asp Ser Ser Pro Asp Ala Ala Arg Ile Arg Val
        35                  40                  45

```
<210> SEQ ID NO 3
<211> LENGTH: 164
<212> TYPE: PRT
<213> ORGANISM: Homo sapiens

<400> SEQUENCE: 3

Ala Arg Leu Asp Val Ala Ser Glu Phe Arg Lys Lys Trp Asn Lys Trp
1               5                   10                  15

Ala Leu Ser Arg Gly Lys Arg Glu Leu Arg Met Ser Ser Ser Tyr Pro
            20                  25                  30

Thr Gly Leu Ala Asp Val Lys Ala Gly Pro Ala Gln Thr Leu Ile Arg
        35                  40                  45

Pro Gln Asp Met Lys Gly Ala Ser Arg Ser Pro Glu Asp Ser Ser Pro
    50                  55                  60

Asp Ala Ala Arg Ile Arg Val Lys Arg Tyr Arg Gln Ser Met Asn Asn
65                  70                  75                  80

Phe Gln Gly Leu Arg Ser Phe Gly Cys Arg Phe Gly Thr Cys Thr Val
                85                  90                  95

Gln Lys Leu Ala His Gln Ile Tyr Gln Phe Thr Asp Lys Asp Lys Asp
            100                 105                 110

Asn Val Ala Pro Arg Ser Lys Ile Ser Pro Gln Gly Tyr Gly Arg Arg
        115                 120                 125

Arg Arg Arg Ser Leu Pro Glu Ala Gly Pro Gly Arg Thr Leu Val Ser
    130                 135                 140

Ser Lys Pro Gln Ala His Gly Ala Pro Ala Pro Ser Gly Ser Ala
145                 150                 155                 160

Pro His Phe Leu

<210> SEQ ID NO 4
<211> LENGTH: 185
<212> TYPE: PRT
<213> ORGANISM: Homo sapiens

<400> SEQUENCE: 4

Met Lys Leu Val Ser Val Ala Leu Met Tyr Leu Gly Ser Leu Ala Phe
1               5                   10                  15

Leu Gly Ala Asp Thr Ala Arg Leu Asp Val Ala Ser Glu Phe Arg Lys
            20                  25                  30

Lys Trp Asn Lys Trp Ala Leu Ser Arg Gly Lys Arg Glu Leu Arg Met
        35                  40                  45

Ser Ser Ser Tyr Pro Thr Gly Leu Ala Asp Val Lys Ala Gly Pro Ala
    50                  55                  60

Gln Thr Leu Ile Arg Pro Gln Asp Met Lys Gly Ala Ser Arg Ser Pro
65                  70                  75                  80

Glu Asp Ser Ser Pro Asp Ala Ala Arg Ile Arg Val Lys Arg Tyr Arg
                85                  90                  95

Gln Ser Met Asn Asn Phe Gln Gly Leu Arg Ser Phe Gly Cys Arg Phe
            100                 105                 110

Gly Thr Cys Thr Val Gln Lys Leu Ala His Gln Ile Tyr Gln Phe Thr
        115                 120                 125

Asp Lys Asp Lys Asp Asn Val Ala Pro Arg Ser Lys Ile Ser Pro Gln
    130                 135                 140

Gly Tyr Gly Arg Arg Arg Arg Arg Ser Leu Pro Glu Ala Gly Pro Gly
145                 150                 155                 160
```

```
Arg Thr Leu Val Ser Ser Lys Pro Gln Ala His Gly Ala Pro Ala Pro
                165                 170                 175

Pro Ser Gly Ser Ala Pro His Phe Leu
            180                 185
```

WORKFLOW FOR RISK ASSESSMENT AND PATIENT MANAGEMENT USING PROCALCITONIN AND MIDREGIONAL-PROADRENOMEDULLIN

FIELD OF THE INVENTION

The present invention is in the field of clinical diagnostics. Particularly, the present invention relates to the assessment of severity of a subject being suspected of an infection or having an infection, who may have physiological signs or increased risk factors for infection, in particular from an infectious disease by determination of the levels of Procalcitonin (hereinafter: PCT) and/or proadrenomedullin (hereinafter: proADM)) (SEQ ID No: 3) or a partial peptide or fragment thereof, in particular midregional proadrenomedullin (MR-proADM) (SEQ ID No: 2), in a sample of a patient and the invention is related to a workflow hereto. Moreover, the invention refers to the assessment related to an infection like ruling out/in a patient and stratification, risk assessment, in particular to avoid rehospitalisation and mortality e.g., within the hospital or post discharge.

Due to the assessed severity clinical decisions are ruled like administration or discharge to or from a clinical site as well as initiation and/or change or stop of treatment such as antibiotics, oxygen, fluids and/or improved monitoring and/or initiation of further diagnostics routes to improve the assessment of the diagnosis of the patient and related treatment.

BACKGROUND OF THE INVENTION

PCT is known to be a marker for bacterial infection and sepsis. High blood or serum levels of this peptide prohormone are indicative for severe infections.

PCT reflects the severity of a bacterial infection and is in particular used to monitor progression of infection into sepsis, severe sepsis, or septic shock. It is possible to use PCT to measure the activity of the infection-associated systemic inflammatory response, to control success of antibacterial therapy, and to estimate prognosis (Assicot et al. 1993. Lancet 341:515-8; Clec'h C et al. 2004. Crit Care Med 32:1166-9; Le et al. 2004. Yonsei Med J 45:29-37; Meisner et al. 2005. Curr Opin Crit Care 11:473-480; Wunder et al. 2004. Inflamm Res 53: 158-163). The increase of PCT levels in patients with sepsis correlates with mortality (Oberhoffer et al. 1999. Clin Chem Lab Med 37:363-368).

During bacterial infections, plasma PCT concentrations are typically above 0.25 ng/ml and PCT concentrations can be elevated above the normal range but below the concentrations, which have been known so far to be associated with bacterial infections requiring antibacterial treatment, and that these PCT concentrations are associated with a prognosis of adverse events in these patients (Sinnig et al. 2011. Circ J 75:1184-1191; Kelly et al. 2010. Biomarkers 15:325-331). Moreover, as a cut-off for the presence of a bacterial infection or sepsis, a level of >0.1 ng/ml PCT is indicative.

PCT has already been used for therapy guidance of antibiotics in patients with symptoms of infections (e.g., impaired breathing or respiratory rate (e.g., shortness of breath, or cough), abnormal body temperature (below 36° C. or above 38° C. (fever)), impaired digestive system (e.g., diarrhoea, nausea or vomiting), urinary problems, impaired circulation (e.g., rapid pulse, pain, inflammatory signs)). In patients presenting at the emergency department (ED) with symptoms of lower respiratory tract infections, PCT was measured and only patients with PCT concentrations >0.25 ng/mL or >0.5 ng/mL were treated with antibiotics (Christ-Crain et al. 2004. Lancet 363:600-7). In patients with community-acquired pneumonia (CAP) antibiotic treatment was based on serum PCT concentrations (strongly discouraged at PCT concentrations <0.1 ng/mL; discouraged at PCT concentrations <0.25 ng/mL; encouraged at PCT concentrations >0.25 ng/mL, and strongly encouraged at PCT concentrations >0.5 ng/mL; a delta of 50-80% decrease of PCT indicates a time point for stopping the application of antibiotics) (Christ-Crain et al. 2006. Am J Resp Crit Care Med 174:84-93; Schuetz et al. 2009. JAMA 302 (10) 1059-1066). PCT guidance substantially reduced antibiotic use in CAP without deterioration of patient's outcome. Similarly, PCT-guided therapy using the same decision thresholds as described above, also markedly reduced antibiotic use for acute respiratory tract infections in primary care without compromising patients' outcome (Briel et al. 2008. Arch Intern Med 168:2000-7; Burkhardt et al. 2010. Eur Resp J Express; doi: 10.1183/09031936.00163309).

Hence, it is advisable to determine the PCT level in a sample of a bodily fluid from a patient suffering from an infectious disease before starting a potentially harmful antibiotic therapy. High blood or serum PCT levels indicate the presence of a severe bacterial infection or even sepsis and requires the treatment of the respective patient with antibiotics. A PCT value lower than 0.1 ng/mL indicates a non-infectious disease, a non-bacterial infection, but also an early phase of bacterial infection. A re-measurement within the next 6-12, or at least next 24 hours are recommended to rule out a bacterial infection within the decision to admit a patient into the hospital. This patient group was ignored in the past.

Furthermore, prior art describes how to determine proAdrenomedullin (proADM) and Adrenomedullin in diagnosis (EP0622458B1, Lewis L K, Smith M W, Yandle T G, Richards A M, Nicholls M G. Adrenomedullin (1-52) measured in human plasma by radioimmunoassay: plasma concentration, adsorption, and storage. Clin Chem 1998; 44:571-7; Ueda S, Nishio K, Minamino N, Kubo A, Akai Y, Kangawa K, et al. Increased plasma levels of adrenomedullin in patients with systemic inflammatory response syndrome. Am J Respir Crit Care Med 1999; 160:132-6; Kobayashi K, Kitamura K, Etoh T, Nagatomo Y, Takenaga M, Ishikawa T, et al. Increased plasma adrenomedullin levels in chronic congestive heart failure. Am Heart J 1996; 131:994-8; Kobayashi K, Kitamura K, Hirayama N, Date H, Kashiwagi T, Ikushima I, et al. Increased plasma adrenomedullin in acute myocardial infarction. Am Heart J 1996; 131:676-80.), in particular for the purpose of diagnosing sepsis (EP121600B1).

MR-proADM is disclosed in EP1488209B1 for diagnostic purposes (Struck J, Tao C, Morgenthaler N G, Bergmann A. Identification of an Adrenomedullin precursor fragment in plasma of sepsis patients. Peptides 2004; 25: 1369-72; Morgenthaler N G, Struck J, Alonso C, Bergmann A. Measurement of mid-regional pro-adrenomedullin in plasma with an immunoluminometric assay. Clin Chem 2005; 51:1823-9; Christ-Crain M, Morgenthaler N G, Stolz D, Muller C, Bingisser R, Harbarth S, et al. Pro-adrenomedullin to predict severity and outcome in community-acquired pneumonia [ISRCTN04176397]. Crit Care 2006; 10:R96; Christ-Crain M, Morgenthaler N G, Struck J, Harbarth S, Bergmann A, Muller B. Mid-regional pro-adrenomedullin as a prognostic marker in sepsis: an observational study. Crit Care 2005; 9: R816-24).

A combination of PCT with an additional risk assessment and prognostic aid, which focuses on the overall condition of the patient independently of the infection, can maximize patient safety and physician confidence in guiding the appropriate therapy and treatment (Schuetz P, Mueller B. The role of immune and metabolic biomarkers for improved management of sepsis patients. Expert Rev Clin Immunol. September 2014; 10(9):1255-1262).

MR-proADM and its precursor proADM provide a more accurate and rapid risk assessment of the patient's septic condition in both the Emergency Department (ED) and Intensive Care Unit (ICU) (Travaglino F, De Berardinis B, Magrini L, et al. Utility of Procalcitonin (PCT) and Mid regional pro-Adrenomedullin (MR-proADM) in risk stratification of critically ill febrile patients in Emergency Department (ED). A comparison with APACHE II score. BMC Infect Dis. 2012; 12:184), as well as additionally assessing the risk of developing further clinical complications which might arise as a result of the original septic condition, which can include blood clot formation, tissue death, hypoxia, impaired organ blood flow, and ultimately, organ dysfunction and failure. Indeed, tissue hypoxia may occur even when normal organ blood flow is observed, making it extremely difficult to detect.

However, there is need for an improved, particularly fast assessment of a patient, who presented to a clinical site like the primary care or the ambulance, preferably the ED or the ICU in order to increase patient's clinical safety and support the physician with respect to patient treatment, in particular therapeutic intervention or management or guidance.

DETAILED DESCRIPTION OF THE INVENTION

Definitions

Unless defined otherwise, technical and scientific terms used herein have the same meaning as commonly understood by one of ordinary skill in the art to which this invention belongs. Additional definitions for the following terms and other terms are set forth throughout the specification.

The terms "a," "an," and "the" do not denote a limitation of quantity, but rather denote the presence of "at least one" of the referenced item.

As used in this application, the terms "about" and "approximately" are used as equivalents. Any numerals used in this application with or without about/approximately are meant to cover any normal fluctuations appreciated by one of ordinary skill in the relevant art. As used herein, the term "approximately" or "about," as applied to one or more values of interest, refers to a value that is similar to a stated reference value. In certain embodiments, the term "approximately" or "about" refers to a range of values that fall within 5% or less in either direction (greater than or less than) of the stated reference value unless otherwise stated or otherwise evident from the context (except where such number would exceed 100% of a possible value).

The management of patients in the ED or other clinical sites is associated with a high responsibility of the clinical staff to make fast and right decisions regarding the treatment of the patient, in particular therapeutic intervention or management or guidance. The patient often presents clinical signs of infection that could be very similar to other non-infectious disorders or diseases, like problems with breathing and others that can be related to a non-infectious disorder like asthma or intoxication. The identification of an infection or risk of an infection as well as management regarding further treatment options and the medical triage, related on the severity of the disorder is of high interest. Patients with an increased risk of getting an infection or development of complication (e.g., patients with co-morbidities, and especially elderly or children with impaired immune response) are often not easy to manage. A failure in the assessment of the patient can increase the mortality risk and critical events like sepsis or organ dysfunction. It is important to discharge patients with a low severe disease state, particularly related on a risk of mortality, to avoid complications and/or re-admission into the hospital (post-discharge phase), incl. rehospitalisation.

Therefore, a complex decision tree or matrix supported by marker combinations with one or more cut-off levels (synonymous: threshold levels) may be required to provide a workflow for such a patient's management.

The object of the present invention refers to an improved assessment of severity of an infection of a patient including risk assessment and related clinical decision, particularly discharge, hospitalisation, re-hospitalisation of a post-discharge patient.

The task of the invention is solved by the presented claims.

Surprisingly, it was found that the assessment of severity, by using PCT and pro-ADM, particularly MR-proADM in a complementary manner, and the ruling in/or ruling out of an infection as well as the severity of the disease state allow an improved management of clinical decisions due to a classification of subjects in order to establish a workflow hereto.

Hence, the present invention relates to a method for assessment of severity, in particular of a subject being suspected of an infection or having an infection, comprising the steps of:
  (i) providing a sample of a bodily fluid from said subject;
  (ii) determining in said sample the level of Procalcitonin (PCT) (SEQ ID No. 1) or a fragment thereof or a precursor or fragment thereof having a length of at least 12 amino acid residues, and
  the level of proadrenomedullin (proADM) (SEQ ID No: 3) or a partial peptide or fragment thereof having a length of at least 12 amino acid residues, in particular midregional proadrenomedullin (MR-proADM) (SEQ ID No: 2), or a precursor or fragment thereof having a length of at least 12 amino acid residues, and
  (iii) determining the severity of an infection, particularly of a subject being suspected of an infection or having an infection by comparing said determined PCT level and proADM level, in particular MR-proADM level, or said fragment(s) level thereof with a threshold level.

Surprisingly, the invention refers to the synergy of PCT and pro-ADM or fragment(s) thereof, for the management of patients with an infection or suspected infection and severity of infection. Such patients are to be advantageously discharged from clinical site, in particular ED, if the PCT level is lower than 0.1 ng/mL and pro-ADM or fragment(s) thereof, particularly MR-proADM is lower than 0.88 nmol/L, due to the assessed low severity of a disorder and respectively mortality. Particularly, if PCT is equal or higher than 0.1 ng/ml and pro-ADM or fragment(s) thereof, particularly MR-proADM is lower than 0.88 nmol/L, then the severe risk remain low regarding mortality, independent from an infection and the decision to discharge the patient. In this case the treatment is manageable in an out-patient setting, e.g., by prescription of oral or local drugs like antibiotics instead of invasive application formats.

A preferred embodiment of the invention relates to the following cases of assessed severity. Hence, the invention relates to a method for assessment of severity of an infection, particularly of a subject being suspected of an infection or having an infection, comprising the steps of:

(i) providing a sample of a bodily fluid from said subject;

(ii) determining in said sample the level of Procalcitonin (PCT) or a fragment thereof or a precursor or fragment thereof having a length of at least 12 amino acid residues, and the level of proadrenomedullin (proADM) (SEQ ID No: 3) or a partial peptide or fragment thereof having a length of at least 12 amino acid residues, in particular midregional proadrenomedullin (MR-proADM) (SEQ ID No: 2), or a precursor or fragment thereof having a length of at least 12 amino acid residues, and (iii) determining the severity of an infection, particularly of a subject being suspected of an infection or having an infection by comparing said determined PCT level and proADM level, particularly MR-proADM level, or said fragment(s) level thereof with a threshold level, (iv) wherein said subject has a non-severe infection when said threshold level for PCT is lower than 0.06 ng/ml, more preferred lower than 0.08 ng/ml, most preferred lower than 0.1 ng/ml and said threshold level for proADM or fragment(s) thereof is lower than 0.6 nmol/L more preferred lower than 0.75 nmol/L, most preferred lower than 0.88 nmol/L, and/or (v) wherein said subject has an almost non-severe infection when said threshold level for PCT is lower than 0.06 ng/ml, more preferred lower than 0.08 ng/ml, most preferred lower than 0.1 ng/ml and said threshold level for proADM or fragment(s) thereof is equal or higher than 0.6 nmol/L, more preferred equal or higher than 0.75 nmol/L, most preferred equal or higher than 0.88 nmol/L and not equal or higher than 1.1 nmol/L, more preferred not equal or higher than 1.2 nmol/L, most preferred not equal or higher than 1.28 nmol/L, and/or (vi) wherein said subject has a low severe infection when said threshold level for PCT is lower than 0.06 ng/ml, more preferred lower than 0.08 ng/ml, most preferred lower than 0.1 ng/ml and said threshold level for proADM or fragment(s) thereof is equal or higher than 1.1 nmol/L, more preferred equal or higher than 1.2 nmol/L, most preferred equal or higher than 1.28 nmol/L, and/or (vii) wherein said subject has a very low-severe infection when said threshold level for PCT is equal or higher than 0.06 ng/ml, more preferred equal or higher than 0.08 ng/ml, most preferred equal or higher than 0.1 ng/ml and said threshold level for proADM or fragment(s) thereof is lower than 0.6 nmol/L, more preferred lower than 0.75 nmol/L, most preferred lower than 0.88 nmol/L, and/or (viii) wherein said subject has a low severe infection when said threshold level for PCT is equal or higher than 0.06 ng/ml, more preferred equal or higher than 0.08 ng/ml, most preferred equal or higher than 0.1 ng/ml and said threshold level for proADM or fragment(s) thereof is equal or higher than 0.6 nmol/L, more preferred equal or higher than 0.75 nmol/L, most preferred equal or higher than 0.88 nmol/L, and not equal or higher than 1.1 nmol/L, more preferred not equal or higher than 1.2 nmol/L, most preferred not equal or higher than 1.28 nmol/L, and/or (ix) wherein said subject has a severe infection when said threshold level for PCT is equal or higher than 0.06 ng/ml, more preferred equal or higher than 0.08 ng/ml, most preferred equal or higher than 0.1 ng/ml and said threshold level for proADM or fragment(s) thereof is equal or higher than 1.1 nmol/L, more preferred equal or higher than 1.2 nmol/L, most preferred equal or higher than 1.28 nmol/L.

and/or (x) wherein said subject has a severe infection when said threshold level for PCT is lower than 0.06 ng/ml, more preferred lower than 0.08 ng/ml, most preferred lower than 0.1 ng/ml and said threshold level for proADM or fragment(s) thereof is equal or higher than 1.30 nmol/L more preferred equal or higher than 1.40 nmol/L, most preferred equal or higher than 1.50 nmol/L, and/or (xi) wherein said subject has a severe infection when said threshold level for PCT is lower than 0.06 ng/ml, more preferred lower than 0.08 ng/ml, most preferred lower than 0.1 ng/ml and said threshold level for proADM or fragment(s) thereof is equal or higher than 2.25 nmol/L more preferred equal or higher than 2.50 nmol/L, most preferred equal or higher than 2.75 nmol/L, and/or xii) wherein said subject has a high severe infection when said threshold level for PCT is equal or higher than 0.06 ng/ml, more preferred equal or higher than 0.08 ng/ml, most preferred equal or higher than 0.1 ng/ml and said threshold level for proADM or fragment(s) thereof is equal or higher than 1.30 nmol/L more preferred equal or higher than 1.40 nmol/L, most preferred equal or higher than 1.50 nmol/L, and/or xiii) wherein said subject has a very high severe infection when said threshold level for PCT is equal or higher than 0.06 ng/ml, more preferred equal or higher than 0.08 ng/ml, most preferred equal or higher than 0.1 ng/ml and said threshold level for proADM or fragment(s) thereof is equal or higher than 2.25 nmol/L more preferred equal or higher than 2.50 nmol/L, most preferred equal or higher than 2.75 nmol/L.

The said cases refer to a development of severity from less severe to more severe and most severe which is correlated with a classification of patients.

Therefore, the said cases (iv-xiii) can be distinguished from each other in order to rule out or rule in a patient due to the assessed severity.

Hence, (iv) relates to non-severely infected patients, which shall be ruled out respectively severe infection and having no need for hospitalization and/or the patient is to be discharged.

(v) relates to almost non-severely infected patients, which shall be ruled in respectively with possible infection or a non-infectious severe disorder and having a need for hospitalization without need of isolation.

(vi) relates to low-severely infected patients, which shall be ruled in respectively with possible infection or a non-infectious severe disorder and having a need for hospitalization without need of isolation.

(vii) relates to very low-severely infected patients, which shall be ruled out respectively severe infection and having no need for hospitalization and/or the patient is to be discharged.

(viii) relates to low-severely infected patients, which shall be ruled in respectively severe infection and having a need for hospitalization and need for isolation.

(ix) relates to severely infected patients, which shall be ruled in respectively severe infection and having a strict need for hospitalization, and need for isolation and more frequent monitoring.

(x) relates to severely infected patients, which shall be ruled in respectively possible infection or a high risk of getting an infection or a non-infectious severe disorder with a high risk of developing complications (mortality risk of 25%) and having a need for hospitalization without need of isolation.

(xi) relates to severely infected patients, which shall be ruled in respectively possible infection or a high risk of getting an infection or a non-infectious severe disorder with a very high risk of developing complications (mortality risk of 35%) and having a need for hospitalization, especially the admission to specific units, e.g., the ICU with need of isolation.

(xii) relates to very severely infected patients, which shall be ruled in respectively severe infection and a high risk of developing complications (mortality risk of 25%) and having a strict need for hospitalization and a need of isolation.

(xiii) relates to very severely infected patients, which shall be ruled in respectively severe infection and a very high risk of developing complications (mortality risk of 35%) and having a very strict need for hospitalization and admission to specific units like the ICU and a need of isolation.

Also provided is a method of treating a patient suspected of having an infection, the method comprising the steps of the above aspect, and further (ii) administering an antibiotic to the patient in an ICU setting if the patient is designated as a (x) severely infected patient, (xi) severely infected patient, (xii) very severely infected patient, or (xiii) very severely infected patient.

Also provided is a method of treating a patient suspected of having an infection, the method comprising the steps of the above aspect, and further (ii) administering an antibiotic to the patient in a hospital but outside of an ICU setting if the patient is designated as a (vi) low severely infected patient or a (viii) low severely infected patient.

Also provided is a method of treating a patient suspected of having an infection, the method comprising the steps of:

(i) providing a sample of a bodily fluid from said subject;
(ii) determining in said sample the level of Procalcitonin (PCT) or a fragment thereof or a precursor or fragment thereof having a length of at least 12 amino acid residues, and the level of proadrenomedullin (proADM) (SEQ ID No: 3) or a partial peptide or fragment thereof having a length of at least 12 amino acid residues, in particular midregional proadrenomedullin (MR-proADM) (SEQ ID No: 2), or a precursor or fragment thereof having a length of at least 12 amino acid residues, and
(iii) administering an antibiotic to the patient if the level of PCT is higher than 0.06 ng/ml and the level of proADM is higher than 0.6 nmol/L.

In a preferred embodiment of the invention referring to said ruling-in cases the measurement of PCT has to be repeated preferably within at least 6-12 hours or 24 hours after the first measurement in order to control the status of a possible infection (v, vi, x, xi) or to monitor the response to a treatment, e.g., with antibiotics (vi, vii, viii, xii, xiii). This approach allows to find out the false negative patient group with an early stage of infection or to monitor subjects with increased risk of getting an infection or developing complications.

In a further preferred embodiment of the invention referring to said hospitalized cases (v, vi, vii, viii, ix, x, xi, xii, xiii) the regular re-measurements of PCT and/or proADM or fragment(s) thereof is to be carried out for the monitoring of the severity and therapeutic management in the same sample.

Moreover, the said cases (iv-ix) can be further distinguished from each other, as follows:

If (iv) is applicable, then withholding an antibiotic to the subject.

if (v) is applicable, then withholding an antibiotic to the subject, and optional for clarification or work-up a further determination of PCT within at least 6-12 hours or 24 hours with a patient's sample shall be carried out.

if (vi) is applicable, then administering an antibiotic to the subject, and optional for clarification or work-up a further determination of PCT to identify a viral or fungal infection or an early stage of a bacterial infection.

if (vii) is applicable, then possible withholding an antibiotic, in particular, when the PCT value is below the typical cut off for starting antibiosis, e.g., 0.25 ng/mL to the subject, or start antibiosis when the PCT value is above the typical cut off for starting antibiosis or in patients with increased risk of developing severe infections. The possibly antibiosis can be applied non-invasive, e.g., orally or locally.

if (viii) is applicable, then possible withholding an antibiotic, in particular, when the PCT value is below the typical cut off for starting antibiosis, e.g., 0.25 ng/mL to the subject, or start antibiosis when the PCT value is above the typical cut off for starting antibiosis or in patients with increased risk of developing severe infections and optional for clarification or work-up a further determination of PCT within at least 6-12 hours or 24 hours with a patient's sample shall be carried out.

if one of (ix x, xi, xii, xiii) is applicable, then immediately administering an antibiotic to the subject.

If one of (x, xi, xii, xiii) is applicable, then immediately administering an antibiotic to the subject and for clarification or work-up a further determination of PCT and/or proADM or fragments thereof within at least 6-12 hours or 24 hours with a patient's sample shall be carried out. The patient has a high risk of developing complications (mortality risk 25%-35%), therefore further monitoring, especially regarding organ dysfunction, diagnostic interventions (further biomarker or parameter) and treatment for the stabilization of the patient, e.g., administering oxygen, fluids, antibiotics (intravenous), organ protective actions like renal replacement, mechanical ventilation. The re-measurements support the assessment of treatment efficacy.

The term "possible withholding" means, that withholding is preferred and recommended, i.e. the administration of antibiotics should be avoided or, if required, a low dosage of antibiotics or local treatment is preferred. Just for further clarification or work-up a blood culture test with a patient's sample may be carried out.

The term "possible administering" means, that administering is preferred and recommended, i.e. the administration of antibiotics should be carried out, if required, a low dosage of antibiotics or local treatment in low severe infection is preferred. Just for further clarification or work-up a blood culture test with a patient's sample may be carried out.

In the case of a low sever infection (e.g., regarding complications and mortality), there is need for application of local or oral treatments with drugs like antibiotics or anti-inflammatory drugs.

The clinical staff has the option to discharge the patient. The said application in more severe infections like moderate or severe infections should be preferably systemically like intra-venous or intra-muscular, however, at least oral or local or combinations thereof.

However, in all cases (iv-xiii) a determination of PCT and proADM or fragments thereof may be carried out in order to predict an increasing or decreasing level of PCT and/or proADM or fragment(s) thereof. Hereto, the determination may be conducted separately or simultaneously.

It is preferred, that said re-measurement of PCT and/or proADM or fragments thereof shall apply in a regular manner to avoid false negative infective patients and/or to monitor the treatment response.

Therefore, in a further preferred embodiment of the invention the method for assessment of severity of an infection is suitable for the execution of clinical decisions, particularly advanced treatments and therapies using drugs and other healthy products or additives, in particular antibiotics, oxygen, fluids as well as initiation and/or change or stop of treatment, particularly in intensive care or emergency care or other special care units, to include the decision to hospitalize the subject, including administration or discharge to or from a clinical site including improved monitoring and/or initiation of further diagnostics routes to improve the assessment of the diagnosis of the patient and the related treatment and includes the isolation or non-isolation of a patient for the protection of other patients, particularly hospitalized patients.

Particularly, in all cases (vi., ix, x, xi, xii and xiii.), wherein proADM or fragment(s) thereof are equal or higher than 1.28 nmol/L the following one or more measures i.)-iv.) are applicable:
  i) Conducting blood culture tests from central line and/or different sources and samples (e.g., blood, serum, plasma, urine, CSF, bodily fluids, etc.),
  ii) Conducting oral or intravenous administration of antibiotics according to guidelines, preferably using antibiotic combinations,
  iii) If i) has provided a negative test result and PCT is lower than 0.1 ng/ml then discontinuing administration of antibiotics,
  iv) Monitoring blood test results, like lactate, FBC (complete blood count), U&E (Urea and Electrolytes), LFT (liver function test), CRP, clotting, etc.

However, a determination of PCT and/or proADM or fragments thereof may be carried out in order to predict an increasing or decreasing level of PCT and/or proADM or fragment(s) thereof. Hereto, the determination may be conducted separately or simultaneously. It is preferred, that said re-measurement of PCT and/or proADM or fragments thereof shall apply in a regular manner to avoid false negative infective patients and/or to monitor the treatment response.

In summary, the present invention deals with a workflow and can advantageously manage the risk assessment of a patient being suspected of an infection or having an infection, particularly a patient with an increased risk, who is presented in a clinical site like the primary care or the ambulance, preferably the ED or the ICU. Hereto, a workflow is depicted as FIG. 1.

Moreover, the inventors have found that independent from the determination of a PCT level the following threshold levels for proadrenomedullin (proADM) (SEQ ID No: 3) or a partial peptide or fragment thereof having a length of at least 12 amino acid residues, in particular midregional proadrenomedullin (MR-proADM) (SEQ ID No: 2), or a precursor or fragment thereof having a length of at least 12 amino acid residues, allow the assessment for further clinical decisions.

Hence, in a further aspect, the invention provide a method for assessment of severity of an infection in a subject, comprising the steps of:
  (i) providing a sample of a bodily fluid from said subject;
  (ii) determining independently from a PCT-level, the level of proadrenomedullin (proADM) (SEQ ID No: 3) or a partial peptide or fragment thereof having a length of at least 12 amino acid residues, in particular midregional proadrenomedullin (MR-proADM) (SEQ ID No: 2), or a precursor or fragment thereof having a length of at least 12 amino acid residues, and
  (iii) determining the severity of an infection by comparing said determined proADM level, in particular MR-proADM level, or said fragment(s) level thereof with a threshold level,
    a.) wherein, a threshold level of equal or higher than 0.88 nmol/L refers to a clinical decision to assess a subject/patient for admission to hospital, and/or
    b.) wherein, a threshold level of equal or higher than 1.50 nmol/L refers to the identification of a high risk infectious or non-infectious patient having an approximate mortality rate of at least 25%, and/or
    c.) wherein, a threshold level of equal or higher than 2.75 nmol/L refers to the identification of a very high risk infectious or non-infectious patient having an approximate mortality rate of at least 35%, and/or
    d.) wherein, a threshold level of equal or higher than 2.75 nmol/L refers to a clinical decision to assess a subject/patient for admission to the ICU.

In a further aspect, the invention provides a method for treating a patient with a severe infection comprising the steps of:
  (i) providing a sample of a bodily fluid from said subject;
  (ii) determining independently from a PCT-level, the level of proadrenomedullin (proADM) (SEQ ID No: 3) or a partial peptide or fragment thereof having a length of at least 12 amino acid residues, in particular midregional proadrenomedullin (MR-proADM) (SEQ ID No: 2), or a precursor or fragment thereof having a length of at least 12 amino acid residues, and
  (iii) determining the severity of an infection by comparing said determined proADM level, in particular MR-proADM level, or said fragment(s) level thereof with a threshold level,
  (iv) treating the patient with an antibiotic if the MR-proADM level is equal or higher than 1.50 nmol/L.

In some embodiments, the patient is treated with the antibiotic in the ICU if the MR-proADM level is equal or higher than 2.75 nmol/L.

Particularly, in all cases, wherein proADM or fragment(s) thereof are equal or higher than 1.50 nmol/L the following one or more measures i.)-vi.) are applicable:
  i) Providing oxygen (approximately 15 L/min.) by means of a facemask
  ii) Conducting a fluid bolus therapy, particularly an intravenous bolus for rapid administration of Hartmann's solution (also known as Ringer's lactate solution),
  iii) Conducting blood culture tests from central line, different sources and samples (e.g., urine, CSF, bodily fluids, etc.), iv) Conducting oral or intravenous administration of antibiotics according to guidelines, preferably using antibiotic combinations, v) Monitoring blood test results, like lactate, FBC (complete blood count), U&E (Urea and Electrolytes), LFT (liver function test), CRP, clotting, etc., vi) Monitoring urine output/fluid balance, Particularly, in all cases, wherein proADM or fragment(s) thereof are equal or higher than 2.75 nmol/L the following measure vii.) is applicable additionally:

vii) Monitoring organ dysfunction, incl. checking clinical parameter and other life-sustaining measures.

However, a determination of PCT and/or proADM or fragments thereof may be carried out in order to predict an increasing or decreasing level of PCT and/or proADM or fragment(s) thereof. Hereto, the determination may be conducted separately or simultaneously. It is preferred, that said re-measurement of PCT and/or proADM or fragments thereof shall apply in a regular manner to avoid false negative infective patients and/or to monitor the treatment response.

In summary, the present invention deals with a workflow and can advantageously manage the risk assessment of a patient being suspected of an infection or having an infection, particularly a patient with an increased risk, who is presented in a clinical site like the primary care or the ambulance, preferably the ED or the ICU. Hereto, a workflow is depicted as FIG. 2.

Within the scope of this invention, "Procalcitonin (PCT)" is understood to be a human protein or polypeptide having an amino acid sequence of 1-116 amino acids or 2-116 amino acids (PCT 2-116) or 3-116 amino acids (PCT 3-116) or fragments thereof, as described in EP0656121B1 as well as DE10027954A1. Thus, the length of PCT fragments is at least 12 amino acids, preferably more than 50 amino acids, more preferably more than 110 amino acids. PCT may comprise posttranslational modifications such as glycosylation, liposidation or derivatisation. PCT itself is a precursor of calcitonin and katacalcin. The amino acid sequence of PCT 1-116 is provided in SEQ ID NO:1.

Adrenomedullin (ADM) is encoded as a precursor peptide comprising 185 amino acids ("preproadrenomedullin" or "pre-proADM"), herein provided in SEQ ID NO: 4. ADM and especially the bioactive ADM form comprises the positions 95-146 of the pre-proADM amino acid sequence and is a splice product thereof.

"Proadrenomedullin" ("Pro-ADM") refers to pre-proADM without the signal sequence (amino acids 1 to 21), i.e. to amino acid residues 22 to 185 of pre-proADM. "Midregional proadrenomedullin" ("MR-proADM") refers to the amino acids 45-92 of pre-proADM. The amino acid sequence of MR-proADM is given in SEQ ID NO: 2. It is also envisaged herein that a peptide and fragment thereof of pre-proADM or MR-proADM can be used for the herein described methods. For example, a peptide and fragment thereof can comprise amino acids 22-41 of pre-proADM (PAMP peptide) or amino acids 95-146 of pre-proADM (mature adrenomedullin). A C-terminal fragment of proADM (amino acids 153 to 185 of preproADM) is called adrenotensin. Fragments of proADM peptides or MR-proADM comprise for example 5 or more amino acids. Accordingly, the fragment of proADM may for example be selected from the group consisting of MR-proADM, PAMP, adrenotensin and mature or bioactive adrenomedullin, preferably herein the fragment is MR-proADM.

Hence, fragments of proADM can in the context of the present invention preferably be selected from the group consisting of MR-proADM, PAMP, adrenotensin and mature adrenomedullin, most preferably herein the fragment is MR-proADM.

MR-proADM (EP 1488209B1) demonstrates great plasma stability, which is particularly advantageous. Moreover, the length of MR-proADM fragments is at least 12 amino acids, preferably more than 25 amino acids, more preferably more than 40 amino acids.

Moreover, the invention encompasses the precursor of MR-proADM, namely proADM (SEQ ID No. 3) and pre-proADM (SEQ ID No. 4) as well as fragment(s) thereof. Within the scope of this invention, "proadrenomedullin (proADM)" is understood to be a human protein or polypeptide having an amino acid sequence of 1-185. Thus, the length of proADM fragments is at least 12 amino acids, preferably more than 80 amino acids, more preferably more than 150 amino acids. proADM may comprise posttranslational modifications such as glycosylation, liposidation or derivatisation.

This precursor peptide, which comprises, inter alia, a signal sequence of 21 amino acids at the N-terminus, is referred to as "preproadrenomedullin" (pre-proADM) (Kitamura K, Sakata J, Kangawa K, Kojima M, Matsuo H, Eto T. Cloning and characterization of cDNA encoding a precursor for human adrenomedullin, Biochem Biophys Res Commun 1993: 194:720-725). Pre-proADM comprises 185 amino acids and has the sequence according to SEQ ID No: 4. Known fragments of pre-pro-ADM include PAMP (AA 22-41), MR-pro-ADM (midregional proadrenomedullin) (AA 45-92) (SEQ ID No: 2), ADM (Adrenomedullin) as well as the bioactive form of ADM (AA 95-146), CT-pro-ADM (Adrenotensin) (AA 153-185) and "proadrenomedullin" (proADM) (AA 22-185) (SEQ ID No: 3).

To date, substantially only a few fragments of the peptide fragments formed in the cleavage of the pre-proADM have been more exactly characterized, in particular the physiologically active peptides adrenomedullin (ADM) and "PAMP", a peptide comprising 20 amino acids (22-41) which follows the 21 amino acids of the signal peptide in pre-proADM.

N-terminal fragments of (pre)proAdrenomedulin for diagnosis have also been described in EP0622458B1, such as PAMP (Hashida S, Kitamura K, Nagatomo Y, Shibata Y, Imamura T, Yamada K, et al. Development of an ultra-sensitive enzyme immunoassay for human pro-adrenomedullin N-terminal peptide and direct measurement of two molecular forms of PAMP in plasma from healthy subjects and patients with cardiovascular disease. Clin Biochem 2004; 37: 14-21).

A C-terminal fragment of (pre)proAdrenomedulin for diagnosis has also been described in EP2111552B1, namely CT-pro-ADM (Adrenotensin).

The term "subject or synonymous patient" as used herein refers to a living human or non-human organism that is receiving medical care or that should receive medical care due to a disease, in particular an infection. This includes persons with no defined illness who are being investigated for signs of pathology. Thus, the methods and assays described herein are applicable to both, human and veterinary disease.

The term "patient with an increased risk" in the sense of the invention means particularly a subject having a higher predisposition of getting an infection or developing a complication. Such a patient may have co-morbidities or bodily or mental limitations like autoimmune disorder, diabetes; or defects in the host response like a patient having cancer or loss of the parts of the immune system, e.g., tonsils or being treated with immune-suppressive medication, e.g., after transplantation or HIV; or specific aged groups like elderly or young children or babies; or patients with organ defects like cardiovascular defects, e.g., heart failure, myocarditis, pericarditis, heart valve defect, atherosclerosis, or renal failure, respiratory disorders like COPD, asthma or mucoviscidosis; skin defects, e.g., burns or broader skin inflammation; gastrointestinal defects, e.g., Morbus Crohn, gastritis or gall stones; or liver defects, e.g., hepatitis, liver cirrhosis or drug/alcohol dependency or addiction; or impaired cognitive abilities, e.g., senseless patients or dementia, or taking medications with increased risk of getting severe adverse events; or obesity.

The term "therapeutic intervention or management or guidance" in the sense of the invention means the decision of the medical activities that is based on the clinical picture in combination of the biomarker values or clinical parameters. If the determined PCT and/or ADM values indicates a severe disorder or an infection or an increased risk of getting an infection or complication a medical action, e.g., administration of drugs, e.g., antibiotics and/or medicinal products and/or minimal- or invasive procedures like a surgical procedure and/or organ supportive actions, e.g., application of fluids like Hartmann's solution, blood or blood fragment transfusion, fluid bolus to preserve or recover fluid balance, the circulation and metabolism and/or support breathing with, e.g., oxygen, ventilation (e.g., mechanical ventilation) and/or organ supportive actions, e.g., hemodilution, apheresis renal replacement therapy, e.g., dialysis, immunosuppressive medication, e.g., steroids, pain treatment or isolation of the patient from other patients.

The term "infection" in the sense of the invention means the invasion of an organism's body tissues by disease-causing agents like bacteria, virus, fungus or parasites their multiplication, and the reaction of host tissues to the infectious agents and the toxins they produce. Infectious disease, also known as transmissible disease or communicable disease, is illness resulting from an infection. Such infectious diseases can be preferably treated by administering antibiotics.

The used term "infection" within vi-xiii includes the description of the before mentioned explanation as well as, especially for the cases of PCT below 0.1 ng/mL, early stages of an infection, early stages of an bacterial infection, a non-bacterial infection or other diseases or disorders without infection, that can be assessed as severe by the combinatorial measurement of proADM or fragments thereof, especially equal or higher than 0.88 nmol/L, 1.28 nmol/L, 1.5 nmol/L or 2.75 nmol/L.

In a preferred embodiment, the invention relates to infection caused by bacteria, namely bacterial infection. The complaints and/or symptoms vary depending on the type of bacterium and the location of the bacterial infection. Such complaints and/or symptoms are often overlapping with other diseases or disorders and may be selected from the group comprising complains of headaches, pain that is in a specific part of the body (e.g., the abdomen), dysregulated temperature (>38° C. (fever), >36° C.), a respiratory symptom selected from the group comprising cough, sputum production, dyspnea, tachypnea and pleuritic pain; one finding during auscultation (e.g., rales, crepitation) and one sign of infection (core body temperature >38° C., shivering) and one sign of digestive tract infection (nausea, vomiting, diarrhea), urinary problems, dysregulated circulation like rapid pulse, dysregulated blood pressure, age, impaired immune system and other signs or risk factors for infections.

The classic symptoms of an infection are localized redness, heat, swelling and pain. One of the hallmarks of a bacterial infection is local pain, pain that is in a specific part of the body. For example, if a cut occurs and it is infected with bacteria, pain will occur at the site of the infection. Bacterial throat pain is often characterized by more pain on one side of the throat. An ear infection is more likely to be bacterial if the pain occurs in only one ear.

As stated above, bacterial infection symptoms differ with the type of infections. Depending on the infected area, the symptoms may vary. However, symptoms are always experienced, also when the area is infected even slightly. When bacterial infections are found in respiratory tract, symptoms related to throat and respiration are found. Throat infection is very common in people living in areas with high pollution. Pneumonia is very common in children and elderly people for whom natural immune power will be very less. Bronchitis, sinusitis and pharyngitis are also found in people who suffer from bacterial infections. Colored nasal discharge and headaches are commonly experienced when bacterial infections are in the respiratory tract.

When infections are found in the digestive tract (e.g., gastroenteritis), symptoms are mostly related to digestion problems. Inflammation and pain in the stomach are normally experienced. Diarrhea and vomiting are other symptoms that indicate infections in gastrointestinal tract. Nausea, metabolic imbalance with, e.g., hyperacidity and dehydration, may also be experienced as a result of severe bacterial infection symptoms.

Foul or fishy smell in the vaginal area is a symptom for vaginal infections. Vagina in women has several types of bacteria that do good for the organ. However, if the production of this type of bacteria is irregular, it may lead to infection. Bacterial infection symptoms for infections in urinary tract include itching and pain the urinals. Vaginal infection and infections in urinary tract should not be ignored as they may cause further inflammation in the internal organs like the kidneys.

Meningitis is a serious consequence of bacterial infections in the membranes that cover brain and spinal cord. Though this can be found in adults also, infants are more susceptible to this problem. Common bacterial infection symptoms for meningitis are stiffness in body and neck, headache, irritability, fever or lower than normal temperature, and skin rashes.

Erysipelas is an acute bacterial infection of the dermis, resulting in inflammation. Patients typically develop symptoms including high fevers, shaking, chills headaches, vomiting, and within 48 hours of the initial infection. The erythematous skin lesion enlarges rapidly and has a sharply demarcated raised edge. It appears as a red, swollen, warm, hardened and painful rash, similar in consistency to an orange peel. More severe infections can result in vesicles, bullae, and petechiae, with possible skin necrosis. Lymph nodes may be swollen, and lymphedema may occur. Occasionally, a red streak extending to the lymph node can be seen. The infection may occur on any part of the skin including the face, arms, fingers, legs and toes, but it tends to favor the extremities. Fat tissue is most susceptible to infection, and facial areas typically around the eyes, ears, and cheeks.

Peritonitis is an inflammation of the peritoneum, the serous membrane which lines part of the abdominal cavity and viscera. Peritonitis may be localized or generalized, and may result from infection (often due to rupture of a hollow organ as may occur in abdominal trauma or appendicitis). The main manifestations of peritonitis are acute abdominal pain, abdominal tenderness, and abdominal guarding. The localization of these manifestations depends on whether peritonitis is localized (e.g., appendicitis or diverticulitis before perforation), or generalized to the whole abdomen. In either case pain typically starts as a generalized abdominal pain (with involvement of poorly localizing innervation of the visceral peritoneal layer), and may become localized later (with the involvement of the somatically innervated parietal peritoneal layer). Perforation of a part of the gastrointestinal tract and disruption of the peritoneum are the most common causes of infected peritonitis.

Cholangitis is an inflammation of the bile duct. The most common cause is a bacterial infection. The classic triad of cholangitis is fever, jaundice, and right upper quadrant abdominal pain.

Cholecystitis is an inflammation of the gall bladder and usually presents as a pain in the right upper quadrant. This is usually accompanied by a low-grade fever, vomiting and nausea.

Osteomyelitis means an infection of the bone or bone marrow. In general, microorganisms may infect bone through one or more of three basic methods: via the bloodstream, contiguously from local areas of infection, or penetrating trauma, including iatrogenic causes such as joint replacements or internal fixate on of fractures or root-canaled teeth. Signs and symptoms of an osteomyelitis include fever, pain in the area of the infection, swelling, warmth and redness over the area of the infection.

Hereto, most dangerous bacterial infections lead to sepsis, a critical condition which leads to malfunctioning of organs causing death. Fever and heavy shaking in the body are the bacterial infection symptoms for sepsis. Pains in joints are also felt by patients with sepsis. This has to be treated immediately to stop the infection from spreading to internal organs and to prevent or overcome the cytokine storm and its fatal outcome. In case of sepsis, the patient will be admitted in the hospital for intensive treatment. The term sepsis may alternatively be defined as life-threatening organ dysfunction caused by a dysregulated host response to infection. For clinical operationalization, organ dysfunction can preferably be represented by an increase in the Sequential Organ Failure Assessment (SOFA) score of 2 points or more, which is associated with an in-hospital mortality greater than 10%. Septic shock may be defined as a subset of sepsis in which particularly profound circulatory, cellular, and metabolic abnormalities are associated with a greater risk of mortality than with sepsis alone. Patients with septic shock can be clinically identified by a vasopressor requirement to maintain a mean arterial pressure of 65 mm Hg or greater and serum lactate level greater than 2 mmol/L (>18 mg/dL) in the absence of hypovolemia. Severe sepsis in refers to sepsis associated with organ dysfunction, hypo perfusion abnormality, or sepsis-induced hypotension. Hypo perfusion abnormalities include lactic acidosis, oliguria and acute alteration of mental status. Sepsis-induced hypotension is defined by the presence of a systolic blood pressure of less than about 90 mm Hg or its reduction by about 40 mm Hg or more from baseline in the absence of other causes for hypotension (e.g., cardiogenic shock). Septic shock is defined as severe sepsis with sepsis-induced hypotension persisting despite adequate fluid resuscitation, along with the presence of hypo perfusion abnormalities or organ dysfunction (Bone et al., CHEST 101(6): 1644-55, 1992). The term "sepsis" used herein relates to all possible stages in the development of sepsis.

Accordingly, the severity of infection correlates with symptoms, complaints and adverse events or outcomes, like death, organ dysfunction or other live-threatening conditions of a patient. The methods and kits of the present invention can also comprise determining at least one further biomarker, marker, clinical score and/or parameter in addition to PCT and pro-ADM.

As used herein, a parameter is a characteristic, feature, or measurable factor that can help in defining a particular system. A parameter is an important element for health- and physiology-related assessments, such as a disease/disorder/clinical condition risk, preferably organ dysfunction(s). Furthermore, a parameter is defined as a characteristic that is objectively measured and evaluated as an indicator of normal biological processes, pathogenic processes, or pharmacologic responses to a therapeutic intervention. An exemplary parameter can be selected from the group consisting of Acute Physiology and Chronic Health Evaluation II (APACHE II), the simplified acute physiology score (SAPSII score), quick sequential organ failure assessment score (qSOFA), sequential organ failure assessment score (SOFA score), body mass index, weight, age, sex, IGS II, liquid intake, white blood cell count (especially neutrophilic bandform granulocytes, segmented neutrophils, eosinophils, basophils, monocytes, lymphocytes), erythrocyte count, thrombocyte count, hemoglobin, hematocrit, sodium, potassium, temperature, blood pressure, dopamine, bilirubin, respiratory rate, partial pressure of oxygen, World Federation of Neurosurgical Societies (WFNS) grading, and Glasgow Coma Scale (GCS).

As used herein, terms such as "marker", "surrogate", "prognostic marker", "factor" or "biomarker" or "biological marker" are used interchangeably and relate to measurable and quantifiable biological markers (e.g., specific protein or enzyme concentration or a fragment thereof, specific hormone concentration or a fragment thereof, or presence of biological substances or a fragment thereof) which serve as indices for health- and physiology-related assessments, such as a disease/disorder/clinical condition risk, preferably an adverse event. A marker or biomarker is defined as a characteristic that can be objectively measured and evaluated as an indicator of normal biological processes, pathogenic processes, or pharmacologic responses to a therapeutic intervention. Biomarkers may be measured in a sample (as a blood, plasma, urine, or tissue test).

The at least one further marker and/or parameter of said subject can be selected from the group consisting of a level of lactate, CRP, the sequential organ failure assessment score (SOFA score) of said subject, the simplified acute physiology score (SAPSII) of said subject, the Acute Physiology and Chronic Health Evaluation II (APACHE II) score of said subject and a level of the soluble fms-like tyrosine kinase-1 (sFlt-1), Histone H2A, Histone H2B, Histone H3, Histone H4, calcitonin, Endothelin-1 (ET-1), Arginine Vasopressin (AVP), Atrial Natriuretic Peptide (ANP), Neutrophil Gelatinase-Associated Lipocalin (NGAL), Troponin, Brain Natriuretic Peptide (BNP), C-Reactive Protein (CRP), Pancreatic Stone Protein (PSP), Triggering Receptor Expressed on Myeloid Cells 1 (TREM1), Interleukin-6 (IL-6), Interleukin-1, Interleukin-24 (IL-24), Interleukin-22 (IL-22), Interleukin (IL-20) other ILs, Presepsin (sCD14-ST), Lipopolysaccharide Binding Protein (LBP), Alpha-1-Antitrypsin, Matrix Metalloproteinase 2 (MMP2), Metalloproteinase 2 (MMP8), Matrix Metalloproteinase 9 (MMP9), Matrix Metalloproteinase 7 (MMP7, Placental growth factor (PlGF), Chromogranin A, S100A protein, S100B protein and Tumor Necrosis Factor α (TNFα), Neopterin, pro-arginine vasopressin (AVP, proAVP or Copeptin), atrial natriuretic peptide (ANP, pro-ANP), E-selectin, ICAM-1, VCAM-1, IP-10, CCL1/TCA3, CCL11, CCL12/MCP-5, CCL13/MCP-4, CCL14, CCL15, CCL16, CCL17/TARC, CCL18, CCL19, CCL2/MCP-1, CCL20. CCL21, CCL22/MDC, CCL23, CCL24, CCL25, CCL26, CCL27, CCL28, CCL3, CCL3L3, CCL4, CCL4L1/LAG-1, CCL5, CCL6, CCL7, CCL8, CCL9, CX3CL1, CXCL1, CXCL10, CXCL11, CXCL12, CXCL13, CXCL14, CXCL15, CXCL16, CXCL17, CXCL2/MIP-2, CXCL3, CXCL4, CXCL5, CXCL6, CXCL7/Ppbp, CXCL9, IL8/CXCL8, XCL1, XCL2, FAM19A1, FAM19A2, FAM19A3, FAM19A4, FAM19A5, CLCF1, CNTF, IL11, IL31, IL6, ICAM, Leptin, LIF, OSM, IFNA1, IFNA10, IFNA13, IFNA14, IFNA2, IFNA4, IFNA7, IFNB1, IFNE, IFNG, IFNZ, IFNA8, IFNA5/IFNaG, IFNω/IFNW1, BAFF, 4-1BBL, TNFSF8, CD40LG, CD70, CD95UCD178, EDA-A1, TNFSF14, LTA/TNFB, LTB, TNFa, TNFSF10, TNFSF11, TNFSF12, TNFSF13, TNFSF15, TNFSF4, IL18, IL18BP, IL1A, IL1B, ILF10, ILF3/IL1RA, IL1F5, IL1F6, IL1F7, IL1F8, IL1RL2, IL F9, IL33 or a fragment thereof.

Lactate, or lactic acid, is an organic compound with the formula $CH_3CH(OH)COOH$, which occurs in bodily fluids including blood. Blood tests for lactate are performed to determine the status of the acid base homeostasis in the body. Lactic acid is a product of cell metabolism that can accumulate when cells lack sufficient oxygen (hypoxia) and must turn to a less efficient means of energy production, or when a condition causes excess production or impaired clearance of lactate. Lactic acidosis can be caused by an inadequate amount of oxygen in cells and tissues (hypoxia), for example if someone has a condition that may lead to a decreased amount of oxygen delivered to cells and tissues, such as shock, septic shock or congestive heart failure, the lactate test can be used to help detect and evaluate the severity of hypoxia and lactic acidosis.

C-reactive protein (CRP) is a pentameric protein, which can be found in bodily fluids such as blood plasma. CRP levels can rise in response to inflammation. Measuring and charting CRP values can prove useful in determining disease progress or the effectiveness of treatments.

As used herein, the "sequential organ failure assessment score" or "SOFA score" is one score used to track a patient's status during the stay in an intensive care unit (ICU). The SOFA score is a scoring system to determine the extent of a person's organ function or rate of failure. The score is based on six different scores, one each for the respiratory, cardiovascular, hepatic, coagulation, renal and neurological systems. Both the mean and highest SOFA scores being predictors of outcome. An increase in SOFA score during the first 24 to 48 hours in the ICU predicts a mortality rate of at least 50% up to 95%. Scores less than 9 give predictive mortality at 33% while above 14 can be close to or above 95%.

As used herein, the quick SOFA score (qSOFA) is a scoring system that indicates a patient's organ dysfunction or mortality risk. The score is based on three criteria: 1) an alteration in mental status, 2) a decrease in systolic blood pressure of less than 100 mm Hg, 3) a respiration rate greater than 22 breaths per minute. Patients with two or more of these conditions are at greater risk of having an organ dysfunction or to die.

As used herein, "APACHE II" or "Acute Physiology and Chronic Health Evaluation II" is a severity-of-disease classification scoring system (Knaus et al., 1985). It can be applied within 24 hours of admission of a patient to an intensive care unit (ICU) and may be determined based on 12 different physiologic parameters: AaDO2 or PaO2 (depending on FiO2), temperature (rectal), mean arterial pressure, pH arterial, heart rate, respiratory rate, sodium (serum), potassium (serum), creatinine, hematocrit, white blood cell count and Glasgow Coma Scale.

As used herein, "SAPS II" or "Simplified Acute Physiology Score II" relates to a system for classifying the severity of a disease or disorder (see Le Gall J R et al., A new Simplified Acute Physiology Score (SAPS II) based on a European/North American multicenter study. JAMA. 1993; 270(24):2957-63.). The SAPS II score is made of 12 physiological variables and 3 disease-related variables. The point score is calculated from 12 routine physiological measurements, information about previous health status and some information obtained at admission to the ICU. The SAPS II score can be determined at any time, preferably, at day 2. The "worst" measurement is defined as the measure that correlates to the highest number of points. The SAPS II score ranges from 0 to 163 points. The classification system includes the followings parameters: Age, Heart Rate, Systolic Blood Pressure, Temperature, Glasgow Coma Scale, Mechanical Ventilation or CPAP, PaO2, FiO2, Urine Output, Blood Urea Nitrogen, Sodium, Potassium, Bicarbonate, Bilirubin, White Blood Cell, Chronic diseases and Type of admission. There is a sigmoidal relationship between mortality and the total SAPS II score. The mortality of a subject is 10% at a SAPSII score of 29 points, the mortality is 25% at a SAPSII score of 40 points, the mortality is 50% at a SAPSII score of 52 points, the mortality is 75% at a SAPSII score of 64 points, the mortality is 90% at a SAPSII score of 77 points (Le Gall loc. cit.).

The term "comparing" as used herein in reference to the use of PCT and/or proADM or fragment(s) thereof as markers, refers to comparing the presence or amount of the marker in a patient to its presence or amount in persons known to suffer from, or known to be at risk of, a given condition. A marker level in a patient sample can be compared to a level known to be associated with a specific prognosis. The sample's marker level is said to have been correlated with a prognosis; that is, the skilled artisan can use the marker level to determine whether the patient has a specific risk to suffer from an adverse event, and respond accordingly. Alternatively, the sample's marker level can be compared to a marker level known to be associated with a good outcome (e.g., a low risk to suffer from an adverse event).

The term "sample" as used herein refers to a sample of bodily fluid obtained for the purpose of assessment, diagnosis, prognosis, or evaluation of a subject of interest, treatment guidance such as a patient. Preferred test samples include blood, serum, plasma, cerebrospinal fluid, urine, saliva, sputum, and pleural effusions. In addition, one of skill in the art would realize that some test samples would be more readily analyzed following a fractionation or purification procedure, for example, separation of whole blood into serum or plasma components.

Thus, in a preferred embodiment of the invention the sample is selected from the group comprising a blood sample, a serum sample, a plasma sample, a cerebrospinal fluid sample, a saliva sample and a urine sample or an extract of any of the aforementioned samples. Preferably, the sample is a blood sample, most preferably a serum sample or a plasma sample.

The term "plasma" in the context of the present invention is the virtually cell-free supernatant of blood containing anticoagulant obtained after centrifugation. Exemplary anticoagulants include calcium ion binding compounds such as EDTA or citrate and thrombin inhibitors such as heparinates or hirudin. Cell-free plasma can be obtained by centrifugation of the anticoagulated blood (e.g., citrated, EDTA or heparinized blood), for example for at least 15 minutes at 2000 to 3000 g.

The term "serum" in the context of the present invention is the liquid fraction of whole blood that is collected after the blood is allowed to clot. When coagulated blood (clotted blood) is centrifuged serum can be obtained as supernatant.

The term "urine" is a liquid product of the body secreted by the kidneys through a process called urination (or micturition) and excreted through the urethra.

The term "regular re-measurement" in the sense of the present invention means in a repeated time frame for example every, 6 hours, every 12 hours, highly preferred every 24 hours, every 2 days, every 3 days, every 4 days or preferred in decision processes like before change of hospital sites, discharge, admission or stop or change of therapy.

The term "assessment of severity" in the sense of the present invention means the diagnosis of the onset and monitoring of the progression of the severity and related infection, in particular the detection and marking of the infectious disease at the different stages due to its severity. Moreover, the term "assessment of severity" relates to the grouping of subjects into different risk groups according to their further prognosis, in particular as provided with the defined cases (supra). Hereto, risk assessment also relates to stratification for applying preventive and/or therapeutic measures.

Hence, the term "diagnosis" in the context of the present invention relates to the recognition and detection of an infection in a subject and/or the ruling in or out of an infection and the related severity, particularly a severe infection.

The term "monitoring" relates to keeping track of an already diagnosed infection, infection related disorder or complication or risk, e.g., to analyze the progression of the disease or the influence of a particular treatment on the progression of the infection or infection related disorder or complication or risk as well as the assessment of the response of a treatment. A positive response shifts the marker values to normal ranges and improves the patients' health condition in general, e.g., less pain, improved breathing, no fever etc. and indicated the right therapeutic rail and/or the need of changing, stopping or adding the medical action or the application format (e.g., from intravenous to oral or vice versa), therapeutic procedure/medication or change of medical location (from normal station to the ICU or vice versa or discharge).

The invention further relates to kits, the use of the kits and methods wherein such kits are used. The invention relates to kits for carrying out the herein above and below provided methods. The herein provided definitions, e.g., provided in relation to the methods, also apply to the kits of the invention. In particular, the invention relates to kits for the assessment, risk stratification, monitoring, therapy guidance and/or therapy control of an infection or a suspected infection in said subject.

The sensitivity and specificity of a diagnostic test depends on more than just the analytical "quality" of the test, they also depend on the definition of what constitutes an abnormal result. In practice, Receiver Operating Characteristic curves (ROC curves), are typically calculated by plotting the value of a variable versus its relative frequency in "normal" (i.e. apparently healthy) and "disease" populations (i.e. patients suffering from an infection). Depending on the particular diagnostic question to be addressed, the reference group must not be necessarily "normals", but it might be a group of patients suffering from another disease or condition, from which the diseased group of interest shall be differentiated. For any particular marker, a distribution of marker levels for subjects with and without a disease will likely overlap. Under such conditions, a test does not absolutely distinguish normal from disease with 100% accuracy, and the area of overlap indicates where the test cannot distinguish normal from disease. A threshold is selected, above which (or below which, depending on how a marker changes with the disease) the test is considered to be abnormal and below which the test is considered to be normal. The area under the ROC curve is a measure of the probability that the perceived measurement will allow correct identification of a condition. ROC curves can be used even when test results don't necessarily give an accurate number. As long as one can rank results, one can create a ROC curve. For example, results of a test on "disease" samples might be ranked according to degree (e.g., 1=low, 2=normal, and 3=high). This ranking can be correlated to results in the "normal" population, and a ROC curve created. These methods are well known in the art (See, e.g., Hanley et al. 1982. Radiology 143: 29-36). Preferably, a threshold is selected to provide a ROC curve area of greater than about 0.5, more preferably greater than about 0.7. The term "about" in this context refers to +/−5% of a given measurement.

The horizontal axis of the ROC curve represents (1-specificity), which increases with the rate of false positives. The vertical axis of the curve represents sensitivity, which increases with the rate of true positives. Thus, for a particular cut-off selected, the value of (1-specificity) may be determined, and a corresponding sensitivity may be obtained. The area under the ROC curve is a measure of the probability that the measured marker level will allow correct identification of a disease or condition (e.g., prognosis). Thus, the area under the ROC curve can be used to determine the effectiveness of the test.

In certain embodiments, markers and/or marker panels are selected to exhibit at least about 70% sensitivity, more preferably at least about 80% sensitivity, even more preferably at least about 85% sensitivity, still more preferably at least about 90% sensitivity, and most preferably at least about 95% sensitivity, combined with at least about 70% specificity, more preferably at least about 80% specificity, even more preferably at least about 85% specificity, still more preferably at least about 90% specificity, and most preferably at least about 95% specificity. In particularly preferred embodiments, both the sensitivity and specificity are at least about 75%, more preferably at least about 80%, even more preferably at least about 85%, still more preferably at least about 90%, and most preferably at least about 95%. The term "about" in this context refers to +/−5% of a given measurement.

Threshold levels can be obtained for instance from a Kaplan-Meier analysis, where the occurrence of a disease or the probability of an adverse outcome and/or death is correlated with the, e.g., quintiles, of the respective markers in the population. According to this analysis, subjects with marker levels above the 80th percentile have a significantly increased risk for getting an adverse event according to the invention. This result is further supported by Cox regression analysis with adjustment for classical risk factors. The highest quartile versus all other subjects is highly significantly associated with increased risk for getting a disease or the probability of an adverse outcome and/or death according to the invention.

Other preferred cut-off values are for instance the 90th, 95th or 99th percentile of a reference population. By using a higher percentile than the 80th percentile, one reduces the number of false positive subjects identified, but one might miss to identify subjects, who are at moderate, albeit still increased risk. Thus, one might adapt the cut-off value depending on whether it is considered more appropriate to identify most of the subjects at risk at the expense of also identifying "false positives", or whether it is considered more appropriate to identify mainly the subjects at high risk at the expense of missing several subjects at moderate risk.

Other mathematical possibilities to calculate an individual's risk by using the individual's marker level value and other prognostic laboratory and clinical parameters are for instance the NRI (Net Reclassification Index) or the IDI (Integrated Discrimination Index). The indices can be calculated according to Pencina (Pencina M J, et al.: Evaluating the added predictive ability of a new marker: from area under the ROC curve to reclassification and beyond. Stat Med. 2008; 27:157-172).

Hereto, the mentioned cut-offs of PCT and pro-ADM and the fragment(s) thereof can vary up to 5%, 10%, 15%, 16%, 17% and is due to the diagnostic method and apparatus and the normal, biological variation within the patient population. For instance, the mentioned cut-off of pro-ADM or fragments thereof of 0.88 nmol/L with a variation of 10% comes to an range of 0.792-0.968 nmol/L and shows no overlap with the other mentioned cut-offs.

The preferred detection methods comprise immunoassays in various formats such as for instance mass spectrometry (MS), luminescence immunoassay (LIA), radioimmunoassay (RIA), chemiluminescence- and fluorescence-immunoassays, enzyme immunoassay (EIA), Enzyme-linked immunoassays (ELISA), luminescence-based bead arrays, magnetic beads based arrays, protein microarray assays, rapid test formats such as for instance immunochromatographic strip tests, rare cryptate assay, and automated systems/analyzers, e.g., KRYPTOR assay.

The assays can be homogenous or heterogeneous assays, competitive and non-competitive assays. In a particularly preferred embodiment, the assay is in the form of a sandwich assay, which is a non-competitive immunoassay, wherein the molecule to be detected and/or quantified is bound to a first antibody and to a second antibody. The first antibody may be bound to a solid phase, e.g., a bead, a surface of a well or other container, a chip or a strip, and the second antibody is an antibody which is labeled, e.g., with a dye, with a radioisotope, or a reactive or catalytically active moiety. The amount of labeled antibody bound to the analyte is then measured by an appropriate method. The general composition and procedures involved with "sandwich assays" are well-established and known to the skilled person (The Immunoassay Handbook, Ed. David Wild, Elsevier LTD, Oxford; 3rd ed. (May 2005), ISBN-13: 978-0080445267; Hultschig C et al., Curr Opin Chem Biol. 2006 February; 10(1):4-10. PMID: 16376134, incorporated herein by reference).

In a preferred embodiment the assay comprises two capture molecules, preferably antibodies which are both present as dispersions in a liquid reaction mixture, wherein a first labelling component is attached to the first capture molecule, wherein said first labelling component is part of a labelling system based on fluorescence- or chemiluminescence-quenching or amplification, and a second labelling component of said marking system is attached to the second capture molecule, so that upon binding of both capture molecules to the analyte a measurable signal is generated that allows the detection of the formed sandwich complexes in the solution comprising the sample.

Even more preferred, said labeling system comprises rare earth cryptates or rare earth chelates in combination with fluorescence dye or chemiluminescence dye, in particular a dye of the cyanine type.

In the context of the present invention, fluorescence based assays comprise the use of dyes, which may for instance be selected from the group comprising FAM (5- or 6-carboxyfluorescein), VIC, NED, Fluorescein, Fluoresceinisothiocyanate (FITC), IRD-700/800, Cyanine dyes, such as CY3, CY5, CY3.5, CY5.5, Cy7, Xanthen, 6-Carboxy-2',4', 7',4,7-hexachlorofluorescein (HEX), TET, 6-Carboxy-4',5'-dichloro-2',7'-dimethodyfluorescein (JOE), N,N,N',N'-Tetramethyl-6-carboxyrhodamine (TAMRA), 6-Carboxy-X-rhodamine (ROX), 5-Carboxyrhodamine-6G (R6G5), 6-carboxyrhodamine-6G (RG6), Rhodamine, Rhodamine Green, Rhodamine Red, Rhodamine 110, BODIPY dyes, such as BODIPY TMR, Oregon Green, Coumarines such as Umbelliferone, Benzimides, such as Hoechst 33258; Phenanthridines, such as Texas Red, Yakima Yellow, Alexa Fluor, PET, Ethidiumbromide, Acridinium dyes, Carbazol dyes, Phenoxazine dyes, Porphyrine dyes, Polymethin dyes, and the like.

In the context of the present invention, chemiluminescence based assays comprise the use of dyes, based on the physical principles described for chemiluminescent materials in Kirk-Othmer, Encyclopedia of chemical technology, 4th ed., executive editor, J. I. Kroschwitz; editor, M. Howe-Grant, John Wiley & Sons, 1993, vol. 15, p. 518-562, incorporated herein by reference, including citations on pages 551-562. Preferred chemiluminescent dyes are acridiniumesters.

As mentioned herein, an "assay" or "diagnostic assay" can be of any type applied in the field of diagnostics. Such an assay may be based on the binding of an analyte to be detected to one or more capture probes with a certain affinity. Concerning the interaction between capture molecules and target molecules or molecules of interest, the affinity constant is preferably greater than $10^8$ $M^{-1}$.

In the context of the present invention, "capture molecules" are molecules which may be used to bind target molecules or molecules of interest, i.e. analytes (i.e. in the context of the present invention PCT and fragments thereof and/or pro-ADM or fragments thereof), from a sample. Capture molecules must thus be shaped adequately, both spatially and in terms of surface features, such as surface charge, hydrophobicity, hydrophilicity, presence or absence of lewis donors and/or acceptors, to specifically bind the target molecules or molecules of interest. Hereby, the binding may for instance be mediated by ionic, van-der-Waals, pi-pi, sigma-pi, hydrophobic or hydrogen bond interactions or a combination of two or more of the aforementioned interactions between the capture molecules and the target molecules or molecules of interest. In the context of the present invention, capture molecules may for instance be selected from the group comprising a nucleic acid molecule, a carbohydrate molecule, a PNA molecule, a protein, an antibody, a peptide or a glycoprotein. Preferably, the capture molecules are antibodies, including fragments thereof with sufficient affinity to a target or molecule of interest, and including recombinant antibodies or recombinant antibody fragments, as well as chemically and/or biochemically modified derivatives of said antibodies or fragments derived from the variant chain with a length of at least 12 amino acids thereof.

Moreover, the present invention refers to a computer-based tool for the input and assessment of data, the processing of the related workflow contents or said decision tree or matrix and the output of measured values and management recommendations, e.g., by using artificial intelligence and/or machine learning may be included to support the management of clinical decision, wherein reference data are stored on a computer readable medium and/or employed in the form of computer executable code configured for comparing the determined level of PCT or fragment(s) thereof, and/or the determined level of proADM or fragment(s) thereof, to said reference data and wherein the reference data refer to threshold level as indicated above in the disclosed embodiments of the invention.

Examples and FIGS. 3-7

The invention is further described by the following examples and figures. These examples and figures are not intended to limit the scope of the invention, but represent preferred embodiments of aspects of the invention provided for greater illustration of the invention described herein.

Patients:

The mentioned patients came into the ED with physiological signs or increased risk factors for an infection. A blood samples were collected after admission to the ED (time point 0). Plasma (for MR-proADM) and serum (for PCT) concentrations were measured using a TRACE (Time Resolved Amplified Cryptate Emission) technology in combination with a new sandwich immunoassay (Kryptor Compact Plus Analyser, BRAHMS, Hennigsdorf, Germany). Endpoints of the study were the treatment with especially antibiotics and the 28 day mortality rate.

Statistical Analysis:

Differences in clinical characteristics with regards to 28 day mortality were assessed using the $\chi^2$ test for categorical variables, and depending on distribution normality, either Student's t-test or the Mann-Whitney U test for continuous variables. Normally and non-normally distributed variables were expressed in terms of mean (standard deviation) and median [first quartile-third quartile], respectively. The association between antibiotic guidance, severity of a disease state, especially infection as well as the prediction of mortality within 28 days with each biomarker other clinical parameters and score was assessed using, e.g., area under the receiver operating characteristic curves (AUROC), logistic and Cox regression analysis. Logistic regression models were created using either biomarkers or scores in isolation, or adjusted with variables like mortality rate or treatment, and expressed, e.g., as Odds Ratios (OR) and 95% confidence intervals [95% CI]. A two-sided p<0.05 was considered statistically significant. All data were analyzed using an established statistics software. Software capable of enabling this kind of analysis in order to establish suitable reference levels and cut-offs is available, for example JMP 12, JMP 13, Statistical Discovery, from SAS.

Groups:
The statistical calculation is based on
Group 1 referring to (iv) with
PCT <0.1 and MR-proADM <0.88
N=129
Hospitalisation/admission rate: 33.1%
Antibiotic administration rate: 65.3%
Intravenous antibiotic administration rate: 22.6%
Oral antibiotic administration rate: 41.9%
28 day mortality rate: 0.0%
Group 2 referring to (v) with
PCT <0.1 and MR-proADM >0.88
N=68
Hospitalisation/admission rate: 83.8%
Antibiotic administration rate: 67.7%
Intravenous antibiotic administration rate: 46.2%
Oral antibiotic administration rate: 23.1%
28 day mortality rate: 8.9%
Group 3 referring to (v) with
PCT <0.1 and MR-proADM ≥0.88 and <1.28
N=29
Hospitalisation/admission rate: 82.5%
Antibiotic administration rate: 60.0%
Intravenous antibiotic administration rate: 35.9%
Oral antibiotic administration rate: 20.5%
28 day mortality rate: 5.0%
Group 1b referring to (vii) with
PCT ≥ 0.1 and MR-proADM <0.88
N=106
Hospitalisation/admission rate: 61.3%
Antibiotic administration rate: 87.4%
Intravenous antibiotic administration rate: 32.6%
Oral antibiotic administration rate: 38.9%
28 day mortality rate: 0.0%
Group 2b referring to (viii):
PCT <0.1 and MR-proADM ≥ 0.88
N=419
Hospitalisation/admission rate: 96.2%
Antibiotic administration rate: 92.8%
Intravenous antibiotic administration rate: 81.6%
Oral antibiotic administration rate: 10.4%
28 day mortality rate: 16.0%
Group 3b referring to (viii):
PCT ≥ 0.1 and MR-proADM ≥ 0.88 and <1.28
N=99
Hospitalisation/admission rate: 90.0%
Antibiotic administration rate: 84.3%
Intravenous antibiotic administration rate: 55.1%
Oral antibiotic administration rate: 29.2%
28 day mortality rate: 0.0%
Group 4: PCT ≥ 0.1 and MR-proADM 1.50
N=262
Admission rate: 97.3%
Antibiotic administration rate: 96.0%
Intravenous antibiotic administration rate: 92.2%
Oral antibiotic administration rate: 4.1%
28 day mortality rate: 24.7%
Group 5: PCT 0.1 and MR-proADM ≥ 2.75
N=102
Admission rate: 98.6%
Antibiotic administration rate: 98.1%
Intravenous antibiotic administration rate: 95.9%
Oral antibiotic administration rate: 2.0%
28 day mortality rate: 34.0%
RRT requirement: 15.0%

} Generally done in the ICU

Supplemental oxygen: 61.6%
Group 4: PCT <0.1 and MR-proADM 1.50
N=18
Admission rate: 94.4%
Antibiotic administration rate: 88.9%
Intravenous antibiotic administration rate: 72.2%
Oral antibiotic administration rate: 22.2%
28 day mortality rate: 22.2%
Group 5: PCT <0.1 and MR-proADM 1.50
N=4

BRIEF DESCRIPTION OF THE DRAWINGS

FIG. 3 shows: Kaplan-Meier plot using an optimised MR-proADM cut-off of 0.88 nmol/L showing a complete rule-out 28-day mortality.

FIG. 4 shows a ROC analysis for ADM (black) and PCT (grey) in patients on ED-admission for the prediction of the 28-day mortality.

TABLE 1

Area under the curve (AUC and 95% confidence interval (CI)), sensitivity, specificity, positive predictive value (PPV), negative predictive value (NPV), positive likelihood ratio (LR+), negative likelihood ratio (LR−) and diagnostic odds ratio (OR) from receiver operating characteristics (ROC) analysis with MR-proADM and PCT in patients on ED-admission for the 28-day mortality.

| | Biomarkers and clinical scores | AUC | Cut-off | Sensitivity | Specificity | PPV | NPV | LR+ | LR− | OR |
|---|---|---|---|---|---|---|---|---|---|---|
| ED admission | MR-proADM | 0.84 [0.78-0.89] | 1.50 | 0.80 [0.61-0.92] | 0.79 [0.75-0.82] | 0.15 [0.12-0.18] | 0.99 [0.98-0.99] | 3.74 [2.96-4.72] | 0.25 [0.12-0.52] | 14.7 [5.9-36.7] |
| | PCT | 0.68 [0.59-0.77] | 0.20 | 0.80 [0.61-0.92] | 0.49 [0.45-0.53] | 0.07 [0.06-0.08] | 0.98 [0.96-0.99] | 1.58 [1.30-1.91] | 0.41 [0.20-0.83] | 3.9 [1.6-9.6] |

Table 1 shows a MR-proADM cut-off of 1.5 nmol/1 with an AUC 0.84 (0.78-0.89), a sensitivity of 0.8 [0.61-0.92], a specificity of 0.79 [0.75-0.82], an PPV of 0.15 [0.12-0.18], a NPV of 0.99 [0.98-0.99], a LR+ of 3.74 [2.96-4.72], a LR− of 0.25 [0.12-0.52] and an OR of 14.7 [5.9-36.7]. The table 1 shows a PCT cut-off of 2.0 ng/ml with an AUC 0.68 (0.59-0.77), a sensitivity of 0.8 [0.61-0.92], a specificity of 0.49 [0.45-0.53], an PPV of 0.07 [0.06-0.08], a NPV of 0.98 [0.96-0.99], a LR+ of 1.58 [1.30-1.91], a LR− of 0.41 [0.2-0.83] and an OR of 3.9 [1.6-9.6].

Figure 1:
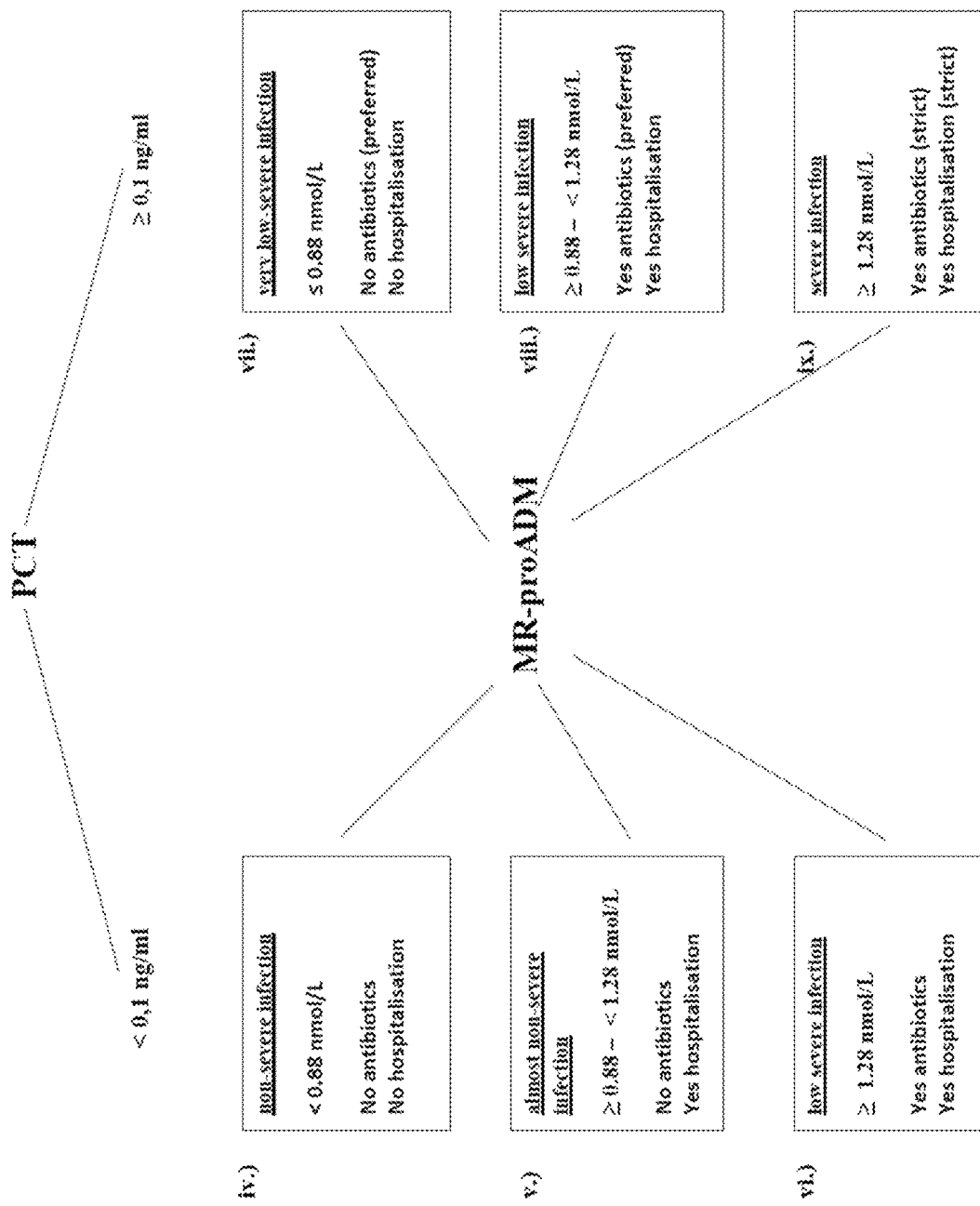
FIG. 1 illustrates a decision workflow diagram.
Figure 2:
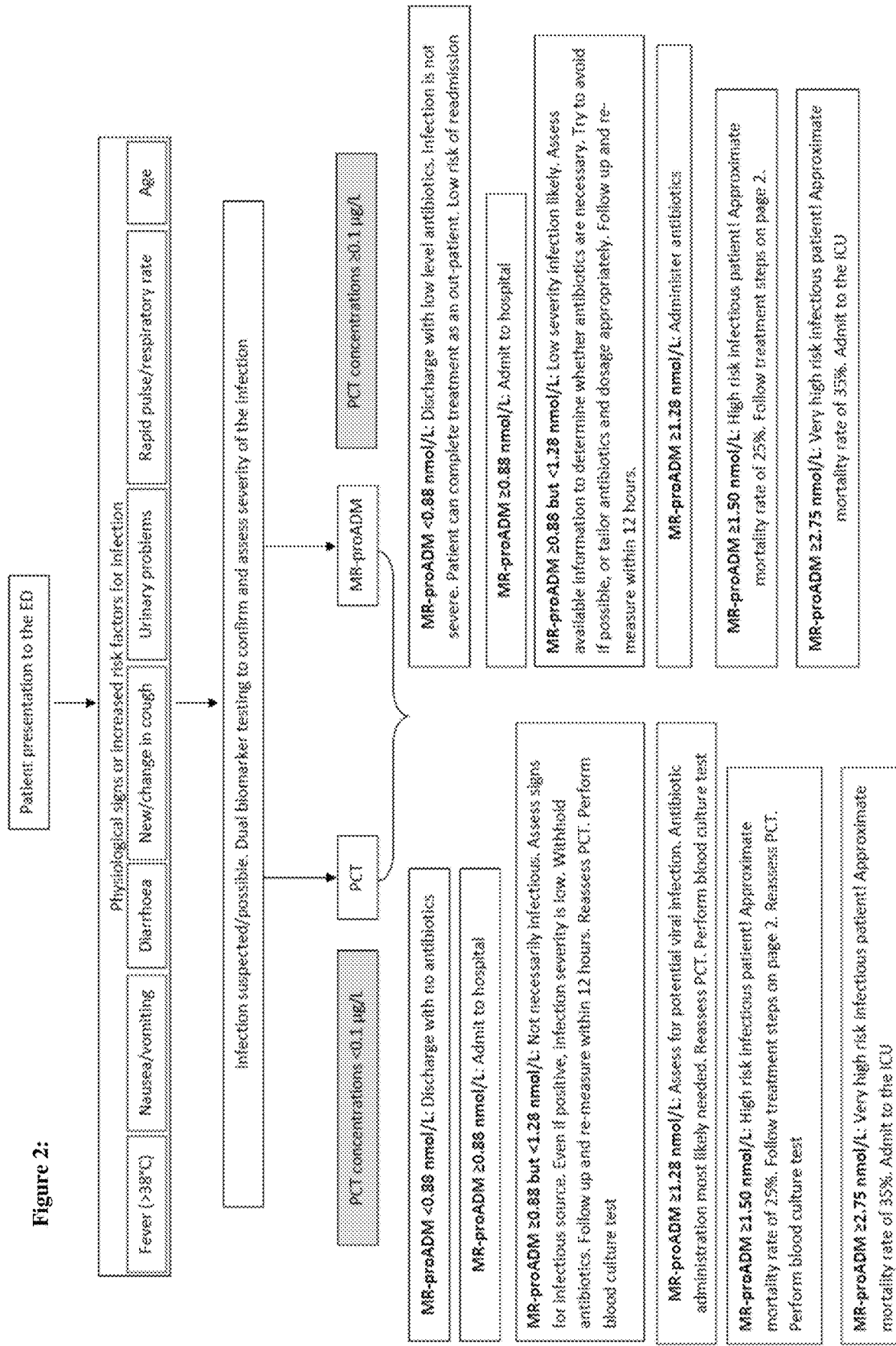
FIG. 2 illustrates a workflow diagram regarding a presenting patient.
Figure 3:
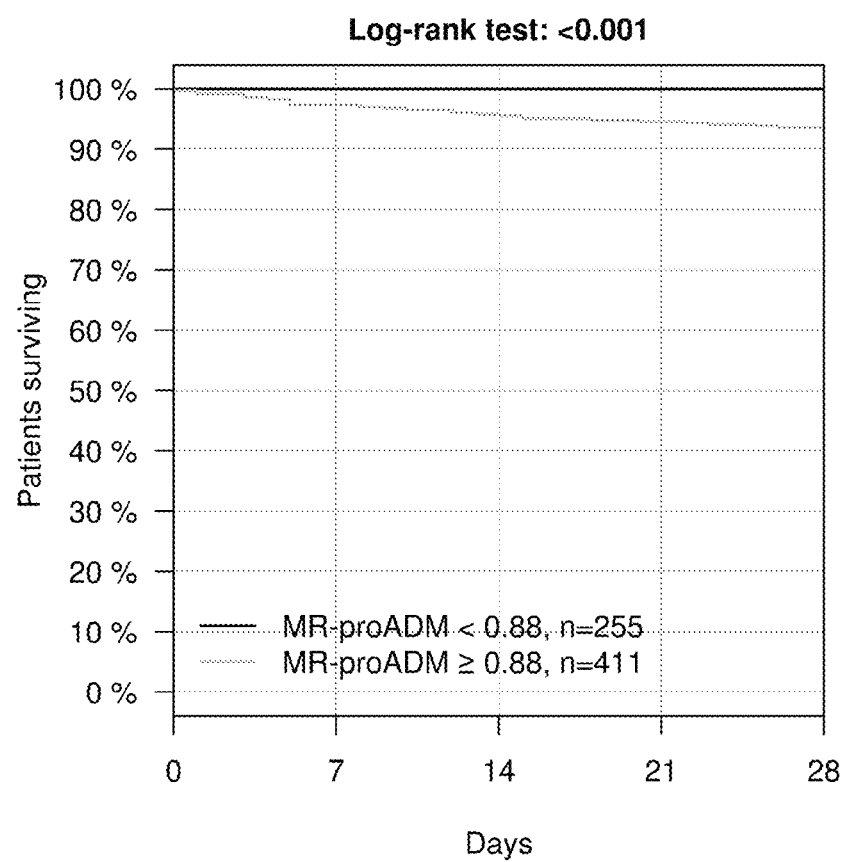
FIG. 3 illustrates a Kaplan-Meier plot.
Figure 4:
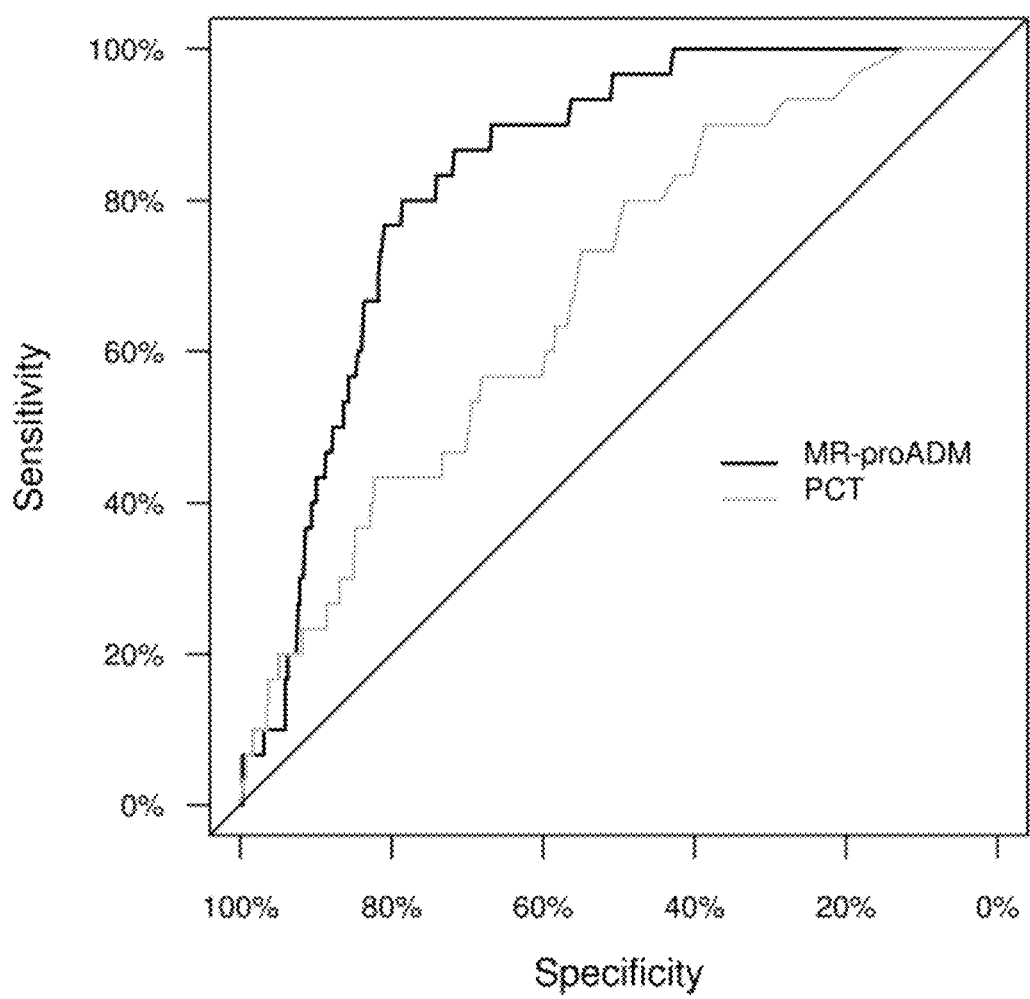
FIG. 4 illustrates a ROC analysis for ADM (black) and PCT (grey) in patients on ED-admission for the prediction of the 28-day mortality.
Figure 5:
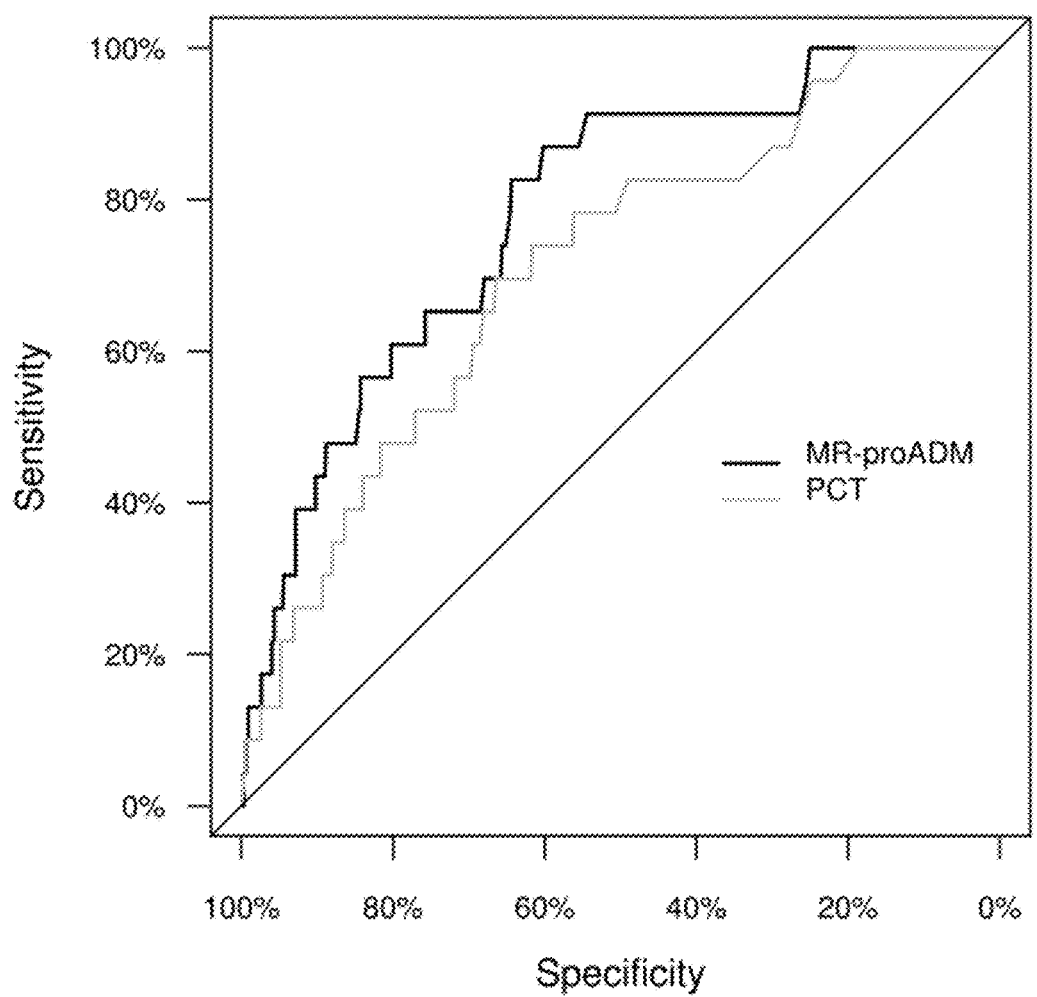
FIG. 5 illustrates a ROC analysis for ADM (black) and PCT (grey) on ED admission for the identification of patients with an increased level of disease severity, as determined by existing organ function (SOFA equal to or above 2 points).

FIG. 5 shows a ROC analysis for ADM (black) and PCT (grey) on ED admission for the identification of patients with an increased level of disease severity, as determined by existing organ function (SOFA equal to or above 2 points).

TABLE 2

Area under the curve (AUC and 95% confidence interval (CI)), sensitivity, specificity, positive predictive value (PPV), negative predictive value (NPV), positive likelihood ratio (LR+), negative likelihood ratio (LR−) and odds ratio (OR) from receiver operating characteristics (ROC) analysis with MR-proADM and PCT in patients on ED-admission with an increased disease severity.

| | Biomarkers and clinical scores | AUC | Cut-off | Sensitivity | Specificity | PPV | NPV | LR+ | LR− | OR |
|---|---|---|---|---|---|---|---|---|---|---|
| ED admission | MR-proADM | 0.78 [0.69-0.87] | 1.28 | 0.87 [0.66-0.97] | 0.60 [0.56-0.64] | 0.07 [0.06-0.09] | 0.99 [0.98-1.00] | 2.18 [1.82-2.63] | 0.22 [0.08-0.62] | 10.1 [2.0-34.3] |
| | PCT | 0.71 [0.61-0.82] | 0.47 | 0.70 [0.47-0.87] | 0.66 [0.63-0.70] | 0.07 [0.05-0.09] | 0.98 [0.97-0.99] | 2.07 [1.55-2.77] | 0.46 [0.25-0.85] | 4.5 [1.8-11.1] |

Table 2 shows a MR-proADM cut-off of 1.28 nmol/l with an AUC 0.78 (0.69-0.87), a sensitivity of 0.87 [0.66-0.97], a specificity of 0.6 [0.56-0.64], an PPV of 0.07 [0.06-0.09], a NPV of 0.99 [0.98-1.00], a LR+ of 2.18 [1.82-2.63], a LR− of 0.22 [0.08-0.62] and an OR of 10.1 [2.0-34.3]. Table 2 shows a PCT cut-off of 0.47 ng/ml with an AUC 0.71 (0.61-0.82), a sensitivity of 0.7 [0.47-0.87], a specificity of 0.66 [0.63-0.70], an PPV of 0.07 [0.05-0.08], a NPV of 0.98 [0.97-0.99], a LR+ of 2.07 [1.55-2.77], a LR− of 0.46 [0.25-0.85] and an OR of 4.5 [1.8-11.1].

Figure 6:
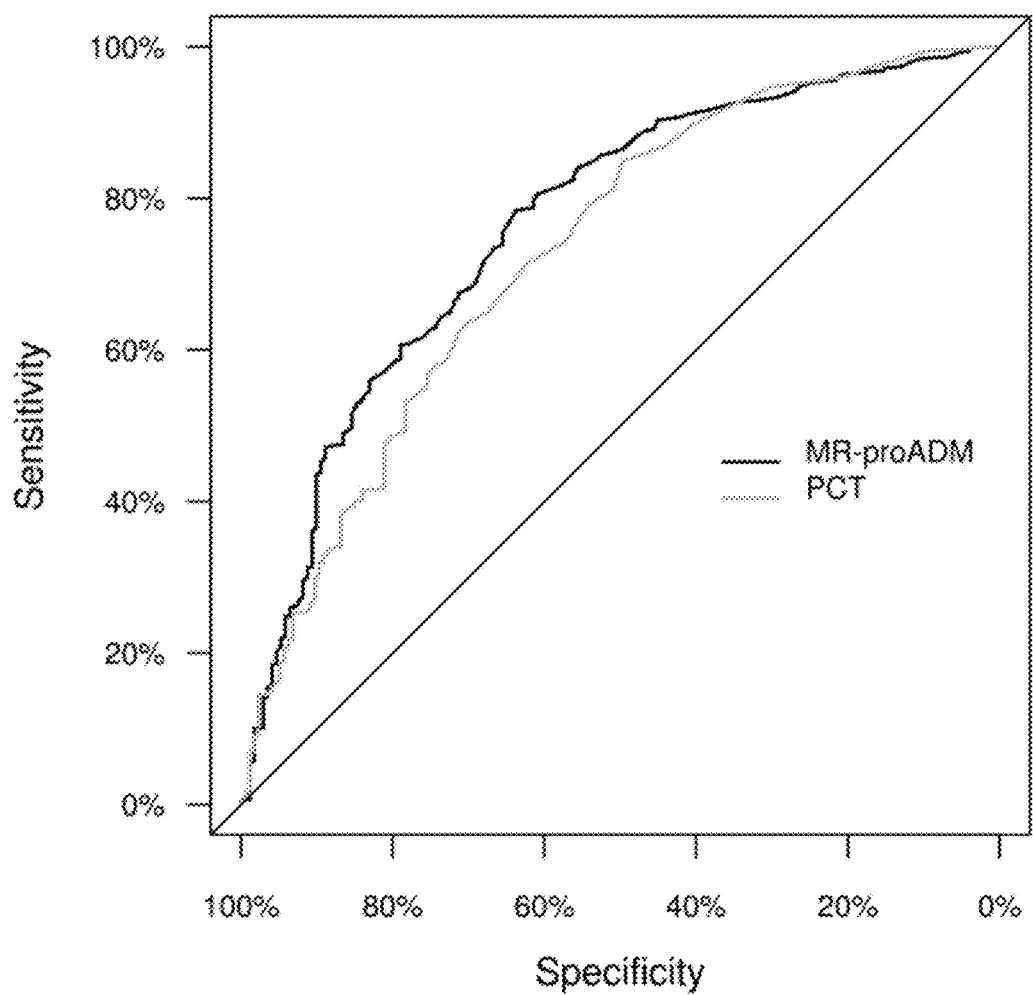
FIG. 6 shows a ROC analysis for ADM (black) and PCT (grey) in patients requiring antibiotic administration upon ED admission.

FIG. 6 shows a ROC analysis for ADM (black) and PCT (grey) in patients requiring antibiotic administration upon ED admission.

TABLE 3

Area under the curve (AUC and 95% confidence interval (CI)), sensitivity, specificity, positive predictive value (PPV), negative predictive value (NPV), positive likelihood ratio (LR+), negative likelihood ratio (LR−) and odds ratio (OR) from receiver operating characteristics (ROC) analysis with MR-proADM and PCT in patients on ED-admission with a requirement for antibiotic administration.

| | Biomarkers and clinical scores | AUC | Cut-off | Sensitivity | Specificity | PPV | NPV | LR+ | LR− | OR |
|---|---|---|---|---|---|---|---|---|---|---|
| ED admission | MR-proADM | 0.77 [0.72-0.81] | 0.88 | 0.78 [0.74-0.82] | 0.64 [0.56-0.71] | 0.86 [0.84-0.88] | 0.50 [0.45-0.56] | 2.16 [1.76-2.65] | 0.34 [0.28-0.42] | 6.4 [4.4-9.3] |
| | PCT | 0.73 | 0.10 | 0.85 | 0.50 | 0.83 | 0.53 | 1.69 | 0.30 | 5.6 |

TABLE 3-continued

Area under the curve (AUC and 95% confidence interval (CI)), sensitivity, specificity, positive predictive value (PPV), negative predictive value (NPV), positive likelihood ratio (LR+), negative likelihood ratio (LR−) and odds ratio (OR) from receiver operating characteristics (ROC) analysis with MR-proADM and PCT in patients on ED-admission with a requirement for antibiotic administration.

| Biomarkers and clinical scores | AUC | Cut-off | Sensitivity | Specificity | PPV | NPV | LR+ | LR− | OR |
|---|---|---|---|---|---|---|---|---|---|
| | [0.69-0.78] | | [0.81-0.88] | [0.42-0.57] | [0.81-0.85] | [0.47-0.60] | [1.45-1.97] | [0.24-0.39] | [3.8-8.2] |

Table 3 shows a MR-proADM cut-off of 0.88 nmol/l with an AUC 0.77 (0.72-0.81), a sensitivity of 0.78 [0.74-0.82], a specificity of 0.64 [0.56-0.71], an PPV of 0.86 [0.84-0.88], a NPV of 0.50 [0.45-0.56], a LR+ of 2.16 [1.76-2.65], a LR− of 0.34 [0.28-0.42], and an OR of 6.4 [4.4-9.3]. The table 3 shows a PCT cut-off of 0.1 ng/ml with an AUC 0.73 (0.69-0.78), a sensitivity of 0.85 [0.81-0.88], a specificity of 0.50 [0.42-0.57], an PPV of 0.83 [0.81-0.85], a NPV of 0.53 [0.47-0.60], a LR+ of 1.69 [1.45-1.97], a LR− of 0.30 [0.24-0.39], and an OR of 5.6 [3.8-8.2].

Figure 7:
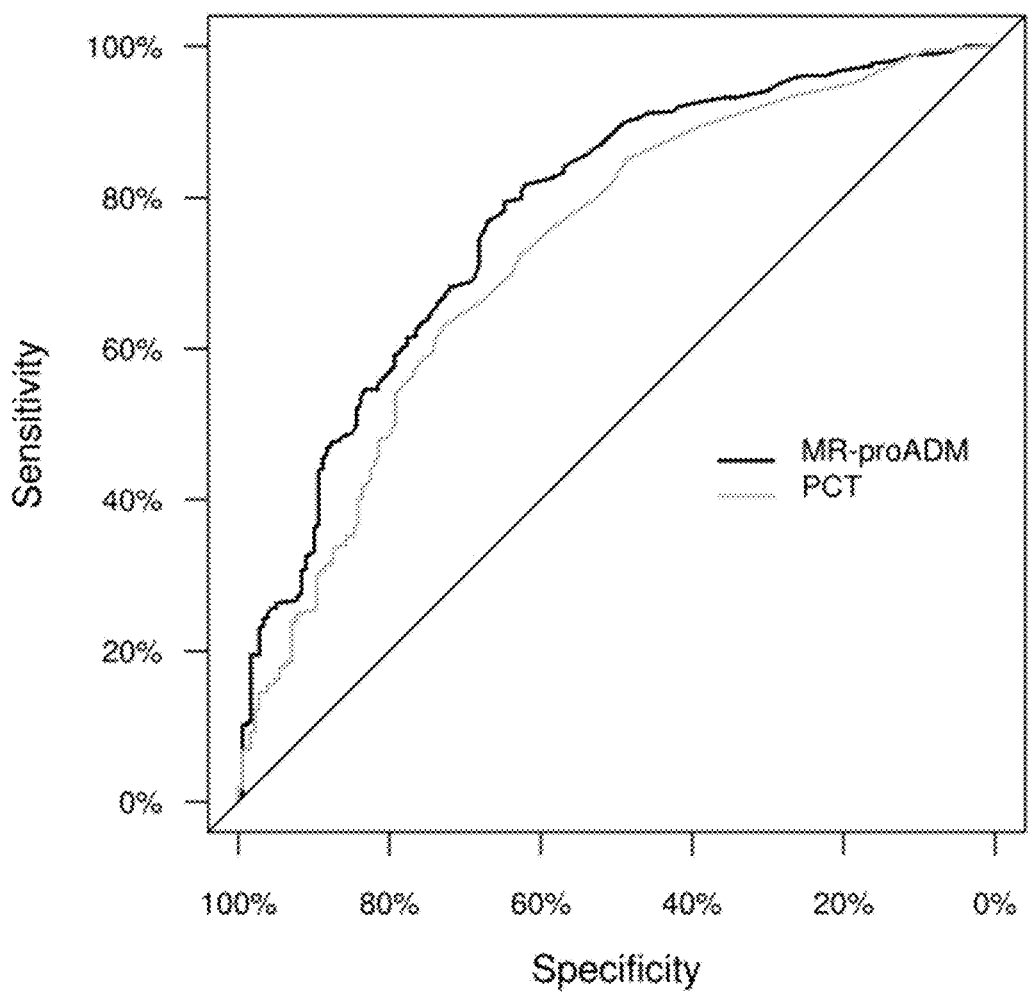
FIG. 7 shows a ROC analysis for ADM (black) and PCT (grey) in patients requiring hospitalization upon ED-admission.

FIG. 7 shows a ROC analysis for ADM (black) and PCT (grey) in patients requiring hospitalization upon ED-admission.

TABLE 4

Area under the curve (AUC and 95% confidence interval (CI)), sensitivity, specificity, positive predictive value (PPV), negative predictive value (NPV), positive likelihood ratio (LR+), negative likelihood ratio (LR−) and odds ratio (OR) from receiver operating characteristics (ROC) analysis with MR-proADM and PCT in patients on ED-admission with a decision for hospitalization.

| | Biomarkers and clinical scores | AUC | Cut-off | Sensitivity | Specificity | PPV | NPV | LR+ | LR− | OR |
|---|---|---|---|---|---|---|---|---|---|---|
| ED admission | MR-proADM | 0.78 [0.74-0.82] | 0.88 | 0.79 [0.76-0.83] | 0.65 [0.57-0.72] | 0.86 [0.83-0.88] | 0.54 [0.49-0.59] | 2.26 [1.84-2.77] | 0.32 [0.26-0.39] | 7.1 [4.9-10.4] |
| | PCT | 0.73 [0.69-0.77] | 0.19 | 0.63 [0.59-0.67] | 0.73 [0.66-0.79] | 0.86 [0.83-0.89] | 0.42 [0.39-0.46) | 2.31 [1.80-2.95] | 0.51 [0.44-0.59] | 4.5 [3.1-6.6] |

Table 4 shows a MR-proADM cut-off of 0.88 nmol/l with an AUC 0.78 (0.74-0.82), a sensitivity of 0.79 [0.76-0.83], a specificity of 0.65 [0.57-0.72], an PPV of 0.86 [0.83-0.88], a NPV of 0.54 [0.49-0.59], a LR+ of 2.26 [1.84-2.77], a LR− of 0.32 [0.26-0.39] and an OR of 7.1 [4.9-10.4]. The table 4 shows a PCT cut-off of 0.19 ng/ml with an AUC 0.73 (0.69-0.77), a sensitivity of 0.63 [0.59-0.67], a specificity of 0.73 [0.66-0.79], an PPV of 0.86 [0.83-0.89], a NPV of 0.42 [0.39-0.46], a LR+ of 2.31 [1.8-2.95], a LR− of 0.51 [0.44-0.59] and an OR of 4.5 [3.1-6.6].

The present invention is not to be limited in scope by the specific embodiments described herein. Indeed, various modifications of the invention in addition to those described herein will become apparent to those skilled in the art from the foregoing description and the accompanying figures. Such modifications are intended to fall within the scope of the appended claims. It is further to be understood that all values are approximate, and are provided for description.

Sequences

SEQ ID NO: 1 (amino acid sequence of PCT):
  1 APFRSALESS PADPATLSED EARLLLAALV QDYVQMKASE LEQEQEREGS

51 SLDSPRSKRC GNLSTCMLGT YTQDFNKFHT FPQTAIGVGA PGKKRDMSSD

101 LERDHRPHVS MPQNAN

SEQ ID NO: 2 (amino acid sequence of MR-pro-ADM):
  1 ELRMSSSYPT GLADVKAGPA QTLIRPQDMK GASRSPEDSS PDAARIRV SEQ ID NO: 3 (amino acid sequence of proADM)
  1 ARLDVASEFR KKWNKWALSR GKRELRMSSS YPTGLADVKA GPAQTLIRPQ

| Sequences |
|---|
| 51 DMKGASRSPE DSSPDAARIR VKRYRQSMNN FQGLRSFGCR FGTCTVQKLA<br><br>101 HQIYQFTDKD KDNVAPRSKI SPQGYGRRRR RSLPEAGPGR TLVSSKPQAH<br><br>151 GAPAPPSGSA PHFL<br><br>SEQ ID NO: 4 (amino acid sequence of pre-proADM)<br>  1 MKLVSVALMY LGSLAFLGAD <u>TARLDVASEF RKKWNKWALS RGKRELRMSS</u><br><br> <u>51 SYPTGLADVK AGPAQTLIRP QDMKGASRSP EDSSPDAARI RVKRYRQSMN</u><br><br>101 <u>NFQGLRSFGC RFGTCTVQKL AHQIYQFTDK DKDNVAPRSK ISPQGYGRRR</u><br><br>151 <u>RRSLPEAGPG RTLVSSKPQA HGAPAPPSGS APHFL</u><br>PAMP 22-41<br>MR-proADM 45-92<br>ADM 95-146<br>CT-proADM 153-185<br>proADM 22-185 |

The invention claimed is:

1. A method of treatment comprising:
   (i) preparing a single sample of a bodily fluid from one subject suspected of an infection, or having an infection;
   (ii) determining in said sample:
      a level of Procalcitonin (PCT) or a fragment or precursor thereof, wherein said fragment or precursor thereof has a length of at least 12 amino acid residues, and
      a level of proadrenomedullin (proADM) or a fragment thereof, having a length of at least 12 amino acid residues, and
   (iii) determining the severity of the infection of the subject, by comparing said determined PCT level and proADM level, or said level of said fragment(s) or precursors, with threshold levels,
   wherein said determined PCT and proADM levels, or said levels of said fragment(s) or precursors, are compared to the PCT and proADM threshold levels of one or more of the following features (iv) to (vi),
   (iv) wherein said subject has a determined level for PCT or fragment or precursor thereof is lower than 0.1 ng/ml, and said determined level for proADM or fragment(s) thereof is equal or higher than 0.88 nmol/L, and not equal or higher than 1.5 nmol/L,
   or,
   (v) wherein said subject has a determined level for PCT or fragment or precursor thereof is lower than 0.1 ng/ml, and said determined level for proADM or fragment(s) thereof is equal or higher than 1.50 nmol/L, and not equal or higher than 2.25 nmol/L,
   or,
   (vi) wherein said subject has a determined level for PCT or fragment or precursor thereof is lower than 0.1 ng/ml, and said determined level for proADM or fragment(s) thereof is equal or higher than 2.25 nmol/L,
   wherein the conditions of at least one of (iv), (v) or (vi) are met, and
   if (iv) is applicable, hospitalizing and administering an antibiotic to the subject,
   if (v) is applicable, hospitalizing and intravenously administering an antibiotic to the subject, and additionally determining a level of PCT or fragment or precursor thereof within 24 hours, or
   if (vi) is applicable, admitting the patient to an intensive care unit (ICU), immediately intravenously administering an antibiotic to the subject and monitoring organ dysfunction of the patient in the ICU.

2. The method according to claim 1, wherein MR-proADM or a fragment thereof having a length of at least 12 amino acid residues is used.

3. The method according to claim 1 for the execution of clinical decisions including therapeutic intervention or management or guidance.

4. The method according to claim 1,
   a) wherein when said determined level for proADM or fragment(s) thereof is equal or higher than 1.50 nmol/L, a high risk infectious patient is determined having an approximate mortality rate of at least 25%, or
   b) wherein when said determined level for proADM or fragment(s) thereof is equal or higher than 2.75 nmol/L, a very high risk infectious patient is determined having an approximate mortality rate of at least 35%.

5. The method according to claim 1, wherein when proADM or fragment(s) thereof, are equal or higher than 1.50 nmol/L, organ dysfunction of the patient is monitored, and one or more of the following measures are applicable:
   i) providing oxygen (approximately 15 L/min.) by means of a facemask,
   ii) conducting a fluid bolus therapy,
   iii) conducting blood culture tests,
   iv) monitoring blood test results, and
   v) monitoring urine output.

6. A method according to claim 1, wherein said sample of a bodily fluid is selected from the group consisting of a blood sample, a serum sample, and a plasma sample.

7. A method comprising:
   preparing a first sample comprising receiving a bodily fluid sample from a subject and adding to said first bodily fluid sample a capture molecule suitable for binding to procalcitonin (PCT) or a fragment or precursor thereof having a length of at least 12 amino acid residues; and
   preparing a second sample comprising receiving the bodily fluid sample from the subject and adding to said bodily fluid sample a capture molecule suitable for binding to proadrenomedullin (proADM) or fragment thereof having a length of at least 12 amino acid residues,
   wherein the first sample has a level of procalcitonin (PCT) or a fragment or precursor thereof having a length of at least 12 amino acid residues, that is lower than 0.1 ng/ml; and the second sample has a level of proadrenomedullin (proADM) or fragment thereof having a length of at least 12 amino acid residues, that is equal to or higher than 0.88 nmol/L,
   or
   wherein the first sample has a level of procalcitonin (PCT) or a fragment or precursor thereof having a length of at least 12 amino acid residues, that is lower than 0.1 ng/ml; and the second sample has a level of proadrenomedullin (proADM) or fragment thereof having a length of at least 12 amino acid residues, that is equal to or higher than 1.5 nmol/L,
   or
   wherein the first sample has a level of procalcitonin (PCT) or a fragment or precursor thereof having a length of at least 12 amino acid residues, that is lower than 0.1 ng/ml; and the second sample has a level of proadrenomedullin (proADM) or fragment thereof having a length of at least 12 amino acid residues, that is equal to or higher than 2.25 nmol/L.

8. A method comprising:

treating a subject with an antibiotic, wherein a bodily fluid sample of the subject has been measured to contain a level of procalcitonin (PCT) or a fragment or precursor thereof having a length of at least 12 amino acid residues, that is lower than 0.1 ng/ml; and a level of proadrenomedullin (proADM) or fragment thereof having a length of at least 12 amino acid residues, that is equal to or higher than 0.88 nmol/L, or wherein a bodily fluid sample of the subject has been measured to contain said subject has been determined to have, in the sample of the subject, a level of PCT or a fragment or precursor thereof having a length of at least 12 amino acid residues, that is lower than 0.1 ng/ml, and a level of proADM or fragment thereof having a length at least 12 amino acid residues, that is equal to or higher than 1.5 nmol/L, or wherein a bodily fluid sample of the subject has been measured to contain said subject has been determined to have, in the sample of the subject, a level of PCT or a fragment or precursor thereof having a length of at least 12 amino acid residues, that is lower than 0.1 ng/ml, and a level of proADM or fragment thereof having a length at least 12 amino acid residues, that is equal to or higher than 2.25 nmol/L.

* * * * *